United States Patent [19]
Carraway et al.

[11] Patent Number: 5,624,816
[45] Date of Patent: Apr. 29, 1997

[54] TRANSMEMBRANE GLYCOPROTEIN ASGP-2: NUCLEOTIDE SEQUENCES AND RECOMBINANT PRODUCTION OF PROTEINS

[75] Inventors: Kermit L. Carraway; Coralie A. Carothers Carraway; Nevis L. Fregien, all of Miami, Fla.

[73] Assignee: University of Miami, Miami, Fla.

[21] Appl. No.: 179,481

[22] Filed: Jan. 3, 1994

Related U.S. Application Data

[63] Continuation of Ser. No. 922,521, Jul. 30, 1992, abandoned.

[51] Int. Cl.$^6$ ............................................. C12N 15/12
[52] U.S. Cl. .................. 435/69.1; 435/69.3; 435/172.1; 435/252.3; 435/325; 435/320.1; 536/23.5; 530/395
[58] Field of Search ........................ 536/23.5, 24.31, 536/24.5; 435/69.1, 69.3, 172.1, 252.3, 240.2, 320.1; 530/395

[56] References Cited

PUBLICATIONS

Falls et al. "ARIA, a Protein That Stimulates Acetylcholine Receptor Synthesis, Is a Member of the New Ligand Family", Cell, vol. 72, pp. 810–815, Mar. 12, 1993.

Marchionni et al, "Glial growth factors are alternatively spliced erbB2 ligands expressed in the nervous system", Nature, vol. 362, pp. 312–318, Mar. 25, 1993.

Carothers Carraway et al. "Association of p185$^{neu}$ with Microfilaments via a Large Glycoprotein Complex in Mammary Carcinoma Microvilli", The Journal of Biological Chemistry, vol. 268, No. 8, pp. 5582–5587, Mar. 15, 1993.

Hull et al. Isolation and partial characterization of ascites sialoglycoprotein–2 of the cell surface sialomucin complex of 13762 rat mammary adenocarcinoma cells, Biochem. J. (1990) 265:121–129.

Petes et al. Isolation of the Neu/HER–2 Stimulatory Ligand: A 44kd Glycoprotein That Induces Differentiation of Mammary Tumor Cells, vol. 80, 1992, 206–216.

Holmes et al. "Indentification of Heregulin, a Specific Activator of p185$^{erB2}$", Science vol. 256, pp. 1205–1210, May 22, 1992.

Wen et al. "Neu Differentiation Factor: A Transmembrane Glycoprotein Containing an EGP Domain and an Immunoglobulin Homolgy Unit," Cell vol. 69, pp. 559–572, May 1, 1992.

Z. Sheng et al J. Cell. Biochem 40:453–66 1989.

Z. Sheng et al. J. Biol. Chem. 265(15):8505–10 May 25, 1990.

D.L. Simmons et al. J. Immunol. 148(1):267–71 Jan. 1, 1992.

R.A. Young et al. PNAS 80:1194–98 Mar. 1983.

M.J.L Ligtenberg et al. J. Biol. Chem 267(9):6171–7 Mar. 25, 1992.

S.R. Hull et al. Biochem J. 265:121–9 1990.

*Primary Examiner*—Stephen G. Walsh
*Assistant Examiner*—Lorraine Spector
*Attorney, Agent, or Firm*—Cushman Darby & Cushman, L.L.P.

[57] ABSTRACT

The present invention relates, in general, to a glycoprotein that is a member of the epidermal growth factor superfamily ASGP-2. In particular, the present invention relates to a DNA segment encoding the glycoprotein; to a recombinant DNA molecule containing the DNA segment; to cells containing the recombinant DNA molecule; to a method of producing the glycoprotein; and to methods of disease diagnosis and therapy that involve the use of the glycoprotein or DNA segment encoding same.

6 Claims, 20 Drawing Sheets

FIG.2A

```
1    GCC CCA GTA GTG TGC TGG TAC AGC CCC GGC CGC TTG ACA TTT GGT GAT    16
     Ala Pro Val Val Cys Trp Tyr Ser Pro Gly Arg Leu Thr Phe Gly Asp

49   CCC CAC ATC ACC ACT TTG GAT AAC GCC AAA TAC ACC TTC AAC GGG CTA    32
     Pro His Ile Thr Thr Leu Asp Asn Ala Lys Tyr Thr Phe Asn Gly Leu

97   GCA TAC TTC CTG CTG GTT CAG GCC CAG GAC AGA AAT TCT TCC TTC CTG    48
     Gly Tyr Phe Leu Leu Val Gln Ala Gln Asp Arg Asn Ser Ser Phe Leu

145  CTG GAG GGC CGC ACT GCC CAG ACT GAT TCT GCC AAT GCC ACG AAC TTC    64
     Leu Glu Gly Arg Thr Ala Gln Thr Asp Ser Ala Asn Ala Thr Asn Phe

193  ATT GCC TTT GCG GCC CAA TAC AAC ACC AGC AGC CTG AAG TCT CCC ATC    80
     Ile Ala Phe Ala Ala Gln Tyr Asn Thr Ser Ser Leu Lys Ser Pro Ile

241  ACA GTT CAG TGG TTT CTT GAC CCC AAT GAC ACA ATC CGA GTT GTA CAC    96
     Thr Val Gln Trp Phe Leu Asp Pro Asn Asp Thr Ile Arg Val Val His

Thr Val Gln Trp Phe Leu Glu Pro Asn Asp Thr Ile Arg Val Val His
```

FIG. 2B

| Pos | | | | | | | | | | | | | | | | | Pos |
|---|---|---|---|---|---|---|---|---|---|---|---|---|---|---|---|---|---|
| 289 | AAT | AAC | CAA | ACG | GTG | GCC | TTT | AAC | ACC | AGC | GAC | ACT | GAA | GAC | TTG | CCC | |
| | Asn | Asn | Gln | Thr | Val | Ala | Phe | Asn | Thr | Ser | Asp | Thr | Glu | Asp | Leu | Pro | 112 |
| 337 | GTA | TTC | AAT | GCC | ACT | GGT | GTC | CTA | ATC | CAA | AAT | GGC | TCC | CAA | GTC | | |
| | Val | Phe | Asn | Ala | Thr | Gly | Val | Leu | Ile | Gln | Asn | Gly | Ser | Gln | Val | | 128 |
| 385 | TCA | GCC | AAC | TTT | GAT | GGG | ACA | GTG | ATT | GCT | CTC | TCC | | | | | |
| | Ser | Ala | Asn | Phe | Asp | Gly | Thr | Val | Ile | Ala | Leu | Ser | | | | | 144 |
| 433 | AAC | ATC | CTT | CAC | GCC | TCC | TCC | AGC | CTG | TCA | GAG | TAC | CGC | AAC | CAC | | |
| | Asn | Ile | Leu | His | Ala | Ser | Ser | Ser | Leu | Ser | Glu | Tyr | Arg | Asn | His | | 160 |
| 481 | ACA | AAG | GGC | CTT | CTG | GGA | GTC | TGG | AAT | GAC | AAT | CCA | GAA | GAT | GAC | TTC | |
| | Thr | Lys | Gly | Leu | Leu | Gly | Val | Trp | Asn | Asp | Asn | Pro | Glu | Asp | Asp | Phe | 176 |
| 529 | AGA | ATG | CCC | AAT | GGC | TCC | ACC | ATC | CCC | TCC | AAC | ACG | TCC | GAG | GAG | ACT | |
| | Arg | Met | Pro | Asn | Gly | Ser | Thr | Ile | Pro | Ser | Asn | Thr | Ser | Glu | Glu | Thr | 192 |

FIG. 2C

```
577  CTT TTC CAC TAT GGA ATG ACA TCG GAA ACT AAC GGG ATA GGC CTC CTT
     Leu Phe His Tyr Gly Met Thr Ser Glu Thr Asn Gly Ile Gly Leu Leu 208

625  GGG GTG AGG ACA GAC CCT CTG CCT TCT GAG TTT ACT CCC ATC TTC TTG
     Gly Val Arg Thr Asp Pro Leu Pro Ser Glu Phe Thr Pro Ile Phe Leu 224

673  TCC CAA CTG TGG AAC AAG AGC GGC GCC GGT GAA GAC TTG ATC TCT GGG
     Ser Gln Leu Trp Asn Lys Ser Gly Ala Gly Glu Asp Leu Ile Ser Gly 240

721  TGC AAC GAG GAC GCA CAG TGC AAG TTT GAC ATC CTG GCC ACA GGA AAC
     Cys Asn Glu Asp Ala Gln Cys Lys Phe Asp Ile Leu Ala Thr Gly Asn 256

769  AGA GAC ATC GGA CAA AGC ACC AAC TCA ATC CTT AGA ACA TTC TGG CAC
     Arg Asp Ile Gly Gln Ser Thr Asn Ser Ile Leu Arg Thr Phe Arg His 272

817  GTG AAT GGC ACG CTC AAC CAG TAC CCA CCC ATC CAC TAC AGC AGC
     Val Asn Gly Thr Leu Asn Gln Tyr Pro Pro Ile His Tyr Ser Ser 288
```

FIG.2D

```
 865 AAG ATT CAA GCC TAC AAG GGG CGA GAA CAG TGG CCA TTG AGA TCA CCA 304
     Lys Ile Gln Ala Tyr Lys Gly Arg Glu Gln Trp Pro Leu Arg Ser Pro

913 GCA ACT CTA AGG ATG TCG TAT TCA GCC TCT CCA ACA AGT GCA GTG GCC 320
     Ala Thr Leu Arg Met Ser Tyr Ser Ala Ser Pro Thr Ser Ala Val Ala

931 TTT GAG CTC TTT GAA AAC GGG AGT TTG CAC GTG GAC ACC AAC ATC CCC 336
     Phe Glu Leu Phe Glu Asn Gly Ser Leu His Val AaspThr Asn Ile Pro 1009 AGA AGA ACG TAC CTG GAG ATT CTA GCA AGG GAT GCT AAG ACT AAC TTG 352
     Arg Arg Thr Tyr Leu Glu Ile Leu Ala Arg Asp Val Lys Thr Asn Leu 1057 TCA TCG GTA CTC CAG CCT GAG ACG GTG GCT TGC TTC TGT AGT AAG GAG 368
     Ser Ser Val Leu Gln Pro Glu Thr Val Ala Cyc Phe Cys Ser Lys Glu 1105 GAA CAG TGT TTG TAC AAC GAG ACC AGC AAA GAG GGC AAC TCT TCC ACT
     Glu Gln Cys Leu Tyr Asn Glu Thr Ser Lys Glu Gly Asn Ser Ser Thr 384
```

FIG. 2E

```
1153  GAG GTG ACC AGC TGC AAG TGC GAT GGG AAC TCC TTC GGC CGC TTG TGT
      Glu Val Thr Ser Cys Lys Cys Asp Gly Asn Ser Phe Gly Arg Leu Cys  400

1201  GAA CAC TCT AAG GAC CTC TGC ACT GAG CCA TGC TTC CCT AAT GTG GAC
      Glu His Ser Lys Asp Leu Cys Thr Glu Pro Cys Phe Pro Asn Val Asp  416

1249  TGC ATT CCT GGG AAG GGC TGT CAG GCC TGT CCT CCA AAC ATG ACT GGA
      Cys Ile Pro Gly Lys Gly Cys Gln Ala Cys Pro Pro Asn Met Thr Gly  432

1297  GAT GGG CGT CAT TGT GTA GCT GTG GAG ATC TCT GAA TTC TGC CAG AAC
      Asp Gly Arg His Cys Val Ala Val Glu Ile Ser Glu Phe Cys Gln Asn  448

1345  CAT TCC TGT CCT GTG AAT TAC TGC TAT AAC CAT GGC CAT TGC GAC ATC
      His Ser Cys Pro Val Asn Tyr Cys Tyr Asn His Gly His Cys Asp Ile  464

1393  TCT GGG CCT CCA GAC TGC CAG CCC ACT TGC ACC TGC GCC CCT GCC TTC
      Ser Gly Pro Pro Asp Cys Gln Pro Thr Cys Thr Cys Ala Pro Ala Phe  480
```

FIG.2F

```
1441  ACT GGT AAC CGC TTC CTG GCC GGG AAC AAT TTC ACT CCC ATC ATC
      Thr Gly Asn Arg Cys Phe Leu Ala Gly Asn Asn Phe Thr Pro Ile Ile  496

1489  TAT AAA GAG CTT CCC TTG AGG ACC ATC ACG CTC TCT CTC AGG GAG GAC
      Tyr Lys Glu Leu Pro Leu Arg Thr Ile Thr Leu Ser Leu Arg Glu Asp  512

1537  GAA AAC GCC TCT GAC AAT GCT GAC GTC AAT GCC TCG GTG GCA AAC CTA
      Glu Asn Ala Ser Asn Ala Asp Val Asn Ala Ser Val Ala Asn Val Leu  528

1585  GAG AAC TTG GAC ATG CGG GCT TTT CTC TCC AAC AGC TTA GTG GAG CTG
      Glu Asn Leu Asp Met Arg Ala Phe Leu Ser Asn Ser Leu Val Glu Leu  544

1633  ATA CGA ACC TCT CCC GGA GCA CCA GTC CTT GGC AAG CCC ATT CAT CAC
      Ile Arg Thr Ser Pro Gly Ala Pro Val Leu Gly Lys Pro Ile His His  560

1681  TGG AAG GTC TCC GTC TCC CAC TTC AAG TAC CGT CCC AGG GGA CCC CTC ATC
      Trp Lys Val Val Ser His Phe Lys Tyr Arg Pro Arg Gly Pro Leu Ile  576
```

FIG. 2G

```
1729 CAC TAT CTG AAC AAC CAA CTG ATA AGC GCC GTG ATG GAG GCC TTC CTC
     His Tyr Leu Asn Asn Gln Leu Ile Ser Ala Val Met Glu Ala Phe Leu  592

1777 CTC CAG GCT CGG CAG GAG AGG AAG AGG AGT GGA GAA GCC AGG AAG
     Leu Gln Ala Arg Gln Glu Arg Lys Arg Ser Gly Glu Ala Arg Lys      608

1825 AAC GTC CGC TTC CCC ATC TCG AGG GCA GAC GTC CAG GAC GGG ATG
     Asn Val Arg Phe Pro Ile Ser Arg Ala Asp Val Gln Asp Gly Met      624

1873 GCC CTG AAC CTA AGT ATG CTG GAC GAG TAC TTC ACG TGC GAT GGC TAC
     Ala Leu Asn Leu Ser Met Leu Asp Glu Tyr Phe Thr Cys Asp Gly Tyr  640

1921 AAA GGC TAC CAC TTG GTC TAC AGC CCC CAG GAT GGC GTC ACC TGT GTG
     Lys Gly Tyr His Leu Val Tyr Ser Pro Gln Asp Gly Val Thr Cys Val  656

1969 TCC CCA AGT GAG GGC TAC TGT CAC AAT GGA GGC CAA TGC AAG CAC
     Ser Pro Ser Glu Gly Tyr Cys His Asn Gly Gly Gln Cys Lys His      672
```

FIG. 2H

```
2017  CTG CCA GAT GGG CCC CAG TGC ACG TGC GCA ACC TTC AGC ATC TAC ACA
      Leu Pro Asp Gly Pro Gln Cys Thr Cys Ala Thr Phe Ser Ile Tyr Thr  688

2065  TCC TGG GGC GAA CGC TGT GAG CAT CTA AGC GTG AAA CTT GGG GCA TTC
      Ser Trp Gly Glu Arg Cys Glu His Leu Ser Val Lys Leu Gly Ala Phe  704

2113  TTC GGG ATC CTC TTT GGA GCC CTG GGT GCC CTC CTA CTG CTG GCC ATC
      Phe Gly Ile Leu Phe Gly Ala Leu Gly Ala Leu Leu Leu Leu Ala Ile  720

2161  TTA GCA TGT GTG GTC TTT CAC TTC TGC GGC TGC TCC ATG AAC AAG TTC
      Leu Ala Cys Val Val Phe His Phe Cys Gly Cys Ser Met Asn Lys Phe  736

2209  TCC TAC CCT CTG GAC TCA GAA CTG TGA GGC CTC GTC CCA GAT GGG CAG
      Ser Tyr Pro Leu Asp Ser Glu Leu ***                              744
```

FIG. 2I

```
2257  CTG CAC CTA GAA TAC CTC AGG ACC CGC CCA CCG GTC TGC CCC TGC TCT
2305  AGG GAG ACT GGA AAG GGC CGA CTC GAT GAA TTG GAT TTG AGA TTC TTC
2353  AAG CAT GAA TAA AGG GAG TGA AAC CAG ACT CTA CCA TTT TAG TAG GCC
2401  ATC GGT ATA GGT TTT CCG GAG ATG AGG AAA TGT AGA GAT GGA TGG ATT
2449  CCT ATA CAG CAC ATG GGA AAG GAT ATT GCC TAT GTA CAC ACA CAC ACA
2497  CAC ACA CAG AGT TAA TGG ATG ACT GGC TTT ATA TTC ACC AAA ATG
2545  TTT TTA CTT ATA AAA CCA GCA TAC TTC TCA TTA AAA TCT ATT TAA ATA
2593  TAA AAA AA
```

FIG. 4

```
C---PVNYCYNHGHC DISGPPDCQPTC T CAPAF---T- GNR C FLAGN    ASGP-2-EGF-I (8-48)
C---SEGYCHNGGQC ---KHLPDGPQC T CATFSIYTSW GER C EHLSVK   ASGP-2EGF-II (217-258)
C---GPGGCGSHARC ---VSDGETAEC Q CLKGFAR-D- GNL C SDIDE    EGF MOUSE (842-880)
C---TESSCLNGGSC ---IDGINGYNC S CLAGY---S- GAN C QY       NOTCH (1026-1058)
C---LENPCSNGGVC ---HQHRESFSC E CPPGF---Y- GNG C EQ       LIN-12 (322-371)
C---ESNPCLNGGSC ---KDDINSYEC W CPFGF---E- GKN C ELOVT    FACTOR IX (97-133)
C---ETSPCQNQGKC ---KDGLGEYTC T CLLGF---E- GKN C ELFTRK   FAXTOR X (78-116)
C---RTNPCLHGGRC ---LEVEGHRLC H CPVGY---T- GPF C DV       FAXTOR XII (165-197)
C---LDNNGCSHVC ---NDLKIGYEC L CPDGFQLVA- QRR C EDIDE     LDL RECEPTOR (318-357)
C---QPWSCSGHGEC ---VGIINNHTC N CDVGY---Y- GPQ C Q        ELAM 1 (56-88)
C---KMNPCLNGGTC ---YPTETSYVC T CVPGY---S- GDQ C ELDFDE   PROTEOGLYCAN CORE (383-415)
C---HSNPCRNGATC ---VDGFNTFRC L CLPSY---V- GAL C EQDTET   PROTEOGLYCAN CORE (422-454)
C PDGPDSGRQFARS CYQDPVTLQ- LACV CDPGY---T- GSR C DDCASG  LAMININ B1 (957-1000)
C---NPYGTMKQQSS C ---NPVTGQ--- C E CLPHV---T- GQD C GACDPG  LAMININ B2 (886-922)
C---DSSLCLNGGTC ---LTGQNDIYC L CPEGF---T- GLV C N        MFGM MOUSE (6-39)
C---SPNPCYNDAKC ---LV Xn YIC Q CPVGY---S- GTH C E        MFGM MOUSE (46-86)
```

FIG. 6

```
EFCQNHSCP----VNYCYNHGHCDISGP--PDCQPTCTCAPAFT-----GNRCFLAGNNFTPI    ASGP1
GVTCVSPCS---EGYCHNGGQCKHL-----PDG-PQCTCATFSIYTSWGERCEHLSVK         ASGP2
NSDSECPLSHDGYCLHDGVCMYIEA----LDKYACNCVVGYI-----GERCQYRDEKWWELR    hEGF
NSYPGCPSSYDGYCLNGGVCMHIES----LDSYTCNCVIGYS-----GDRCQTRDERWWELR    mEGF
NSNTGCPPSYDGYCLNGGVCMYVES----VDRYVCNCVIGYI-----GERCQHRDER         rEGF
QDAPGCPPSHDGFCFHGGVCMHIES----LNTYACNCVIGYV-----GERCEHQDLDWE       gpEGF
VVSHFNDCPDSHTQYCF-HGTCRFLVQ---EDKPACVCHSGYV-----GARCEHADLLA        hTGF alph
VVSHFNKCPDSHTQYCL-HGTCRFLVQ---EEKPACVCHSGYV-----GVRCEHADLLA        rTGF alph
DIPAIRLCGPEGDGYCL-HGDCIHARD---IDGMYCRCSHGYT-----GIRCQHVVLLVDYQRS   VvGP
IVKHVKVCNHDYENYCLNNGTQFTIALDNVSITPFCVCRINYE-----GSRCQFINLVTY       sfGF
IIKRIKLCNDDYKNYCLNNGTCFTVALNNVSLNPFCACHINYV-----GSRCQFINLITIK     mvGF
--KKRDPCLRKYKDFCI-HGECKYVKE---LRAPSCICHPGYH-----GERCHGLSL          hbGF
NRKKNPCNAEFQNFCI-HGECKYIEH---LEAVTCKCQQEYF-----GERCGEKSNKTHSNI   amphi
```

◄180

◄ASGP-2

1 2 3 4 5 6

◄180

◄116

1 2 3   1 2

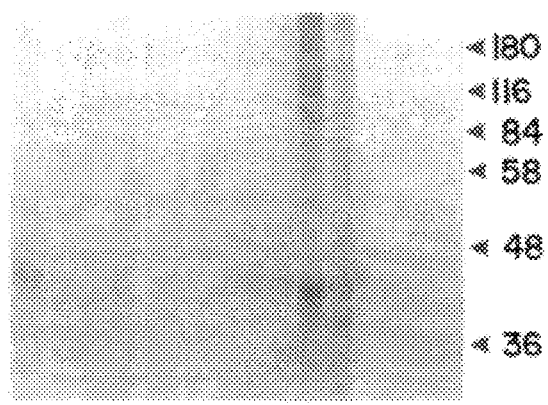
FIG. 12A
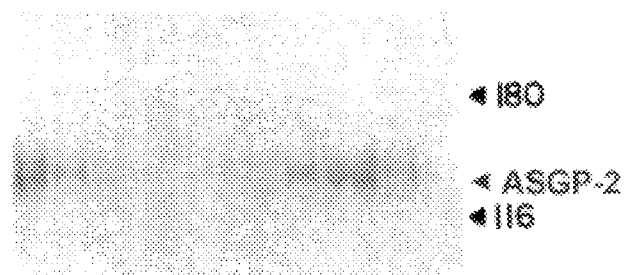
FIG. 12B
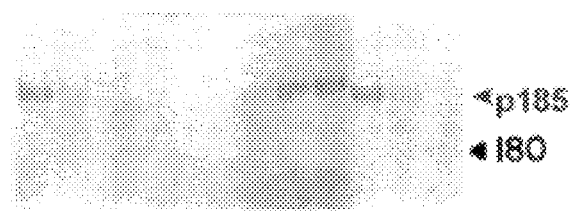
FIG. 12C
2  4  6  8  10  12  14
FIG. 13A  FIG. 13B
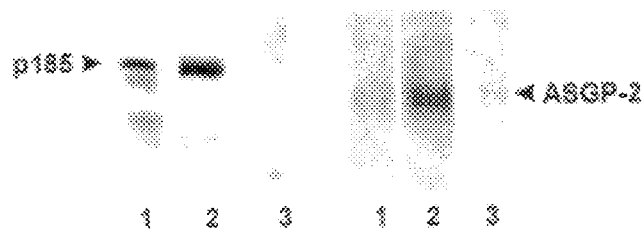
1  2  3    1  2  3

FIG.17A

```
         1         2         3             4     5
EFCQNHSC---PVNYCYNHGHCDISGPPD--CQPTCTCAP----AFTGNRCFLAGNN    ASGP2 EGF1
GVTCVSPC---SEGYCHNGGQCKHLPDGPQ----CTCATFSIYTSWGERCEHLSVK    ASGP2 EGF2
         *                   *
CXXXXXYCLXXSXCXXXXXXXXXXXXXXCXCXX----GYXGXRCXXXXLX          EGF consensus
1         2         3             4     5                6
```

FIG.17B

```
         1         2         3             4     5
EFCQNHSC---PVNYCYNHGHCDISGPPDCQPT--CTCAPAFTGNRCFLAGNNF      ASGP2 EGF1
GTSHLIKCAEKEKTFCVNGGECFTVKDLSNPSRYLCKCQPGFTGARCTENVPMK      NDF
GTShLVKCAEKEKTFCVNGGECFMVKDLSNPSRYLCKCQPGFTGARCTENVPMK      HEREGULIN-α
GTSHLVKCAEKEKTFCVNGGECFMVKDLSNPSRYLCKCPNEFTGDRCQNYVMAS      HEREGULIN-B
GTSHLVKCAEKEKTFCVNGGECFMVKDLSNPSRYLCKGPNEFTGDRCQNYVMAS      GGF
GTSHLTKCDIKQKAFCVNGGECFMVKDLPNPPRYLCRCPNEFTGDRCQNYVMAS      ARIA
         1         2         3             4     5                6
```

FIG.17C

```
         1         2         3             4     5
GVTCVSPCSE---GYCHNGGQC----KHL--PDGPQCTCATFSIYTSWGERC--EHLSVK      ASGP2 EGF2
GTSHLIKCAEKEKTFCVNGGECFTVKDLSNPSRYLCKC--QPGFT--GARCTENVPMK        NDF
GTShLVKCAEKEKTFCVNGGECFMVKDLSNPSRYLCKC--QPGFT--GARCTENVPMK        HEREGULIN-α
GTSHLVKCAEKEKTFCVNGGECFMVKDLSNPSRYLCKC--PNEFT--GDRCQNYVMAS        HEREGULIN-B
GTSHLVKCAEKEKTFCVNGGECFMVKDLSNPSRYLCKC--PNEFT--GDRCQNYVMAS        GGF
GTSHLTKCDIKQKAFCVNGGECFMVKDLPNPPRYLCRC--PNEFT--GDRCQNYVMAS        ARIA
         1         2         3             4     5                6
```

TRANSMEMBRANE GLYCOPROTEIN ASGP-2: NUCLEOTIDE SEQUENCES AND RECOMBINANT PRODUCTION OF PROTEINS

This invention was made with Government support under CA 31695 and GM 08210 from the National Institutes of Health. The Government has certain rights to this invention.

This is a continuation-in-part of application Ser. No. 07/922,521, filed Jul. 30, 1992, now abandoned, the entire contents of which are incorporated herein by reference.

BACKGROUND OF THE INVENTION

1. Field of the Invention

The present invention relates, in general, to a glycoprotein that is a member of the epidermal growth factor superfamily. In particular, the present invention relates to a DNA segment encoding the glycoprotein; to a recombinant DNA molecule containing the DNA segment; to cells containing the recombinant DNA molecule; to a method of producing the glycoprotein; and to methods of disease diagnosis and therapy that involve the use of the glycoprotein or DNA segment encoding same.

2. Background Information

Cell proliferation and differentiation are regulated by polypeptide growth factors (Gospodarowicz and Moran, 1976), which play critical roles in processes leading to both normal and abnormal development (Mercola and Stiles, 1988; Cross and Dexter, 1991). Regulation of cell behavior by growth factors or hormones usually occurs by an endocrine or paracrine mechanism, in which the factor is secreted by one cell and acts at the surface of a different cell (Sporn and Todaro, 1980). In some instances regulation may occur by an autocrine mechanism, in which the growth factor acts on the same cell by which it is secreted (Sporn and Todaro, 1980). For example, secretion of TGF-α by tumor cells with EGF receptors provides an autocrine mechanism for their stimulation (Derynck, 1988). The demonstration of membrane-associated growth factors has led to the proposal of alternative stimulation mechanisms. Massague (1990) has proposed a "juxtacrine" mechanism, an alternative version of paracrine stimulation, in which cell surface growth factor on one cell stimulates growth by interaction with a receptor on the cell surface of a second cell. This mechanism has been observed in cells transfected with cDNA for TGF-α precursor whose cleavage to a secretable product was blocked (Wong et al, 1989; Anklesario et al, 1990). An alternative, auto-stimulatory mechanism has been suggested for transformation by the v-sis oncogene (Bejcek et al, 1989). A mutant v-sis carrying a KDEL endoplasmic reticulum localization signal caused stimulation of the cells even though the growth factor produced was not secreted (Bejcek et al, 1989). This intracellular activation mechanism may also occur with the unmodified oncogene and explain the inability of added antibodies against the sis-encoded protein to block v-sis transformation and the failure of high levels of exogenous v-sis protein to induce transformation of non-transformed cells (Bejcek et al, 1989).

Although growth factors clearly contribute to cancer, the roles that they play are still unclear. PDGF/sis is a potent transforming agent when transfected into fibroblasts. EGF and TGF-α are much less effective, although some cells can be transformed by transfection and selection protocols (Rosenthal et al, 1986; Watanabe et al, 1987). However, over-expression of the EGF receptor led to an amplified growth response to EGF (Kraus et al, 1988). Thus, the oncogenic potential of growth factors may depend on forming a sufficient amount of ligand-receptor complexes in the cell membrane(s). However, there is little existing evidence for such membrane ligand-receptor complexes in tumors.

Sialomucins are large, highly glycosylated glycoproteins containing predominantly O-linked carbohydrate (Carraway et al (1986) Mol. Cell Biochem. 72:109–120). Soluble sialomucins are secreted by epithelial tissues and perform a protective function for the epithelial surfaces (Neutra et al (1987) In Physiology of the Gastrointestinal Tract (Johnson, L. R., ed.) 2nd Ed., pp. 975–1009, Raven Press, New York). A second class of sialomucins is found on the cell surfaces of many carcinomas (Carraway et al (1986) Mol. Cell Biochem. 72:109–120; Carraway et al (1991) Glycobiology 1:131–138) and are postulated to provide protection from immune destruction. Since the sialomucins are long, rod-like structures, they are presumed to extend from the cell surfaces and act as an "anti-immunorecognition" barrier for the tumor cell by masking other cell surface antigens. In support of this hypothesis, the presence of sialomucins has been shown to inhibit binding of antibodies to the histocompatibility complex in mouse TA3-Ha ascites mammary adenocarcinoma cells (Codington et al (1983) Biomembranes 11:207–258), provide resistance to killing of 13762 rat mammary adenocarcinoma cells by natural killer cells (Sherblom et al (1986) Cancer Res. 86:4543–4546; Bharathan et al (1990) Cancer Res. 50:5250–5256) and correlate with metastatic potential in 13762 sublines selected for variable metastasis (Steck et al (1983) Exp. Cell Res. 147:255–267).

As a model system for tumor sialomucin properties and expression, ascites sublines of the 13762 rat mammary adenocarcinoma have been studied in which a cell surface sialomucin designated ASGP-1 is highly overexpressed (Sherblom et al (1980) J. Biol. Chem. 255:783–790). In these cells, the sialomucin is at least 0.5% of the total cell protein (Sherblom et al (1980) J. Biol. Chem. 255:783–790). Moreover, it is indirectly associated with the plasma membrane via a 1:1 molecular complex with a second glycoprotein, ASGP-2 (Sherblom et al (1980) J. Biol. Chem. 255:12051–12059), the membrane-associated component of the complex (Sheng et al (1989) J. Cell Biochem. 40:453–466), which contains primarily N-linked oligosaccharides (Hull et al (1990) Biochem. J. 265:121–129).

Recently, it has been shown that the complex is synthesized as a high $M_r$ precursor, pSMC-1, which is cleaved to yield the two components at an early stage of its transit from the endoplasmic reticulum to the cell surface (Sheng et al (1990) J. Biol. Chem. 265:8505–8510).

The present invention is based, at least in part, on studies resulting in the isolation of cDNAs coding for the carboxyl-terminal portion of pSMC-1, including the entirety of ASGP-2. These studies were undertaken in order to molecularly characterize sialomucin complex expression, its association with the cell surface and its function. The amino acid sequence derived from this cDNA shows the possible cleavage site between the ASGP-1 and ASGP-2 molecules and correlates with the biochemical properties previously demonstrated for ASGP-2, the membrane-associated glycoprotein (Hull et al (1990) Biochem. J. 265:121–129). Surprisingly, this amino acid sequence has also been found to contain two segments with strong similarities to EGF-like domains (Davis (1990) New Biologist 2:410–419). Such domains have been found not only in the growth factors (Carpenter et al (1990) J. Biol. Chem. 265:7709–7712; Appella et al (1988) FEBS Lett. 231:1–4), but also in blood coagulation proteins (Furie et al (1988) Cell 53:505–518), cell-cell adhesion factors (Bevilacqua et al (1989) Science 243:1160–1164), extracellular matrix proteins (Engel (1989) FEBS Lett. 21:1–7) and cell lineage markers for early development (Maine et al (1990) BioEssays 12:265–271). The presence of these domains in the tumor cell surface complex indicates that they perform similar proliferative/recognition functions in these highly metastatic tumor cells.

SUMMARY OF THE INVENTION

The present invention relates to a glycoprotein that functions in autocrine growth control, and thus in the formation and progression of tumor growth.

It is an object of this invention to provide a DNA segment encoding such a glycoprotein.

It is another object of the present invention to provide a recombinant method of producing the glycoprotein.

It is a further object to provide methods for cancer diagnosis and therapy that involve the use of the above glycoprotein and/or DNA segment.

It is yet a further object to provide methods for neural cell regeneration that involve the use of the above glycoprotein and/or DNA segment.

Further objects and advantages of the present invention will be clear from the description that follows.

BRIEF DESCRIPTION OF THE DRAWINGS

FIGS. 2A–2I. Nucleotide sequence of ASGP-2 cDNA clones. The nucleotide sequence of ASGP-2 cDNA is shown (SEQ ID NO: 1; SEQ ID NO:97) with the deduced amino acid sequence (SEQ ID NO: 2) shown below the triplet codons. The amino acid identities with protein sequencing data are indicated in the boxed area. The amino terminus is in the first box and the sequence deduced from the CNBr fragment is in the second box. The hydrophobic, putative transmembrane sequence is indicated by the double underline. Twenty-four potential asparagine-linked glycosylation sites are shown by the single underline. The two EGF-like repeats are shown in hatched boxes. The potential polyadenylation sequences are in bold face.

FIG. 4. Alignment of the EGF-like domains with similar domains in other proteins. The amino acid sequences of selected EGF-like domains are shown, followed by the name of the protein in which they are found. The hatched regions indicate the positions of the highly conserved cysteine residues and other highly conserved amino acids among the ASGP-2 EGF-like repeats and the other EGF-like sequences. (ASGP-2-EGF-I: SEQ ID NO:3 and SEQ ID NO:4; ASGP-2-EGF-II: SEQ ID NO:5 and SEQ ID NO:6; ECG MOUSE: SEQ ID NO:7, SEQ ID NO:8, and SEQ ID NO:9) NOTCH, D. melanogaster neurogenic locus notch protein (SEQ ID NO:10, SEQ ID NO:11, and SEQ ID NO:12); LIN-12 (SEQ ID NO:13, SEQ 10:14, and SEQ ID:15), C. elegans lin-12 protein precursor; FACTORS IX (SEQ ID NO:16, SEQ ID NO:17, and SEQ ID NO:18), X (SEQ ID NO:19, SEQ ID NO:20, and SEQ ID NO:21) and XII (SEQ ID NO:22, SEQ ID NO:23, and SEQ ID NO:24), bovine coagulation factors; LDL Receptor (SEQ ID NO:25, SEQ ID NO:26, and SEQ ID NO:27), human low density lipoprotein receptors; ELAM-1 (SEQ ID NO:28, SEQ ID NO:29, and SEQ ID NO:30), mouse endothelial leukocyte adhesion molecule; PROTEOGLYCAN CORE, human chondroitin sulfate proteoglycan core protein (2 domains) (SEQ ID NO:31 through SEQ ID NO:36); LAMININ B1 and LAMININ B2 (SEQ ID NO:37 through SEQ ID NO:43); MFGM, (SEQ ID NO:44 through SEQ ID NO:49) mouse milk fat globule membrane protein.

FIG. 6. Comparison of ASGP-2 EGF-like domains with active members of the EGF family. The hatched regions indicate the positions of the highly conserved cysteine residues and other amino acids in the EGF-like domains found in proteins with growth factor activity. (ASGP1: SEQ ID NO:50 through SEQ ID NO:53; ASGP2:SEQ ID NO:54 through SEQ ID NO:56) hEGF (SEQ ID NO:57 through SEQ ID NO:59), mEGF (SEQ ID NO:60 through SEQ ID NO:62), rEGF (SEQ ID NO:63 through SEQ ID NO:65) and gpEGF (SEQ ID NO:66 through SEQ ID NO:68), human, mouse, rat and guinea pig epidermal growth factors; hTGF alpha (SEQ ID NO:69 through SEQ ID NO:72) and rTGF alpha (SEQ ID NO:73 through SEQ ID NO:76), human and rat transforming growth factor alphas; vvGF (SEQ ID NO:77 through SEQ ID NO:80), Vaccinia virus growth factor; sTGF (SEQ ID NO:81 and SEQ ID NO:82), shope fibroma virus growth factor; mvGF (SEQ ID NO:83 and SEQ ID NO:84), Myoma virus growth factor; hbGF (SEQ ID NO:85 through SEQ ID NO:88), heparin-binding growth factor; amphi (SEQ ID NO:89 through SEQ ID NO:92), amphiregulin.

FIGS. 12A–C. Fractionation of ASGP-2 and p185 from Triton-solubilized microvillar membranes on sucrose density gradients. Membranes were prepared, solubilized and fractionated as previously described (Carraway et al, 1993). Fractions were analyzed by Coomassie blue staining (panel A), and immunoblotting with anti-ASGP-2 (panel B) and anti-p185 (panel C). Note the co-migration of ASGP-2 with the TMC fractions near the bottom of the gradient.

FIGS. 13A and B. Co-immunoprecipitation ASGP-2 and p185 from gradient fractions of Triton-solubilized microvillar membranes. Gradient fractions 10–12 from FIG. 12 were immunoprecipitated with anti-ASGP-2 (panel A) and anti-p185 (panel B). The immunoprecipitates were analyzed by SDS PAGE and immunoblotting. Panel A, anti-p185 immunoblots; lane 1, microvillar membranes; lane 2, rabbit anti-ASGP-2 immunoprecipitate; lane 3, rabbit pre-immune serum; lane 4, DHFR/G8 membranes; Panel B, anti-ASGP-2 immunoblots; lane 1, microvillar membranes; lane 2, mouse anti-p185 immunoprecipitate; lane 3, mouse nonimmune serum.

FIG. 17 A. Sequence comparisons of the two EGF-like domains of ASGP-2 EGF1 (SEQ ID NO:98 through SEQ ID NO:101), ASGP2 (SEQ ID NO:102 through SEQ ID NO:104), EGF consensus (SEQ ID NO:105 and SEQ ID NO:106).

FIGS. 17 B and C. Comparisons of the ASGP-2 EGF-like domains with NDF/heregulin/ARIA/GGF. Numbers 1–6 denote the cysteine residues used for alignment. The residue identities are noted by double-underlining and the unaligned cysteines are marked with X's. FIG. 17B corresponds to the following sequence identifiers: ASGP2 EGF1 (SEQ ID NO:107 through SEQ ID NO:109), NDF (SEQ ID NO:110), HEREGULIN-α (SEQ ID NO:111), HEREGULIN-β (SEQ ID NO:112), GGF (SEQ ID NO:112), ARIA (SEQ ID NO:113); and FIG. 17C corresponds to the following sequence identifiers, ASGP EGF2 (SEQ ID NO:114) through SEQ ID NO:118), NDF (SEQ ID NO:119 through SEQ ID NO:121), HEREGULIN-α (SEQ ID NO:122, SEQ ID NO:120, SEQ ID NO:121), HEREGULIN-β (SEQ ID NO:122 through SEQ ID NO:124), GGF (SEQ ID NO:122 through SEQ ID NO:124), ARIA (SEQ ID NO:125, SEQ ID NO:123, SEQ ID NO:124).

DETAILED DESCRIPTION OF THE INVENTION

Figure 1:
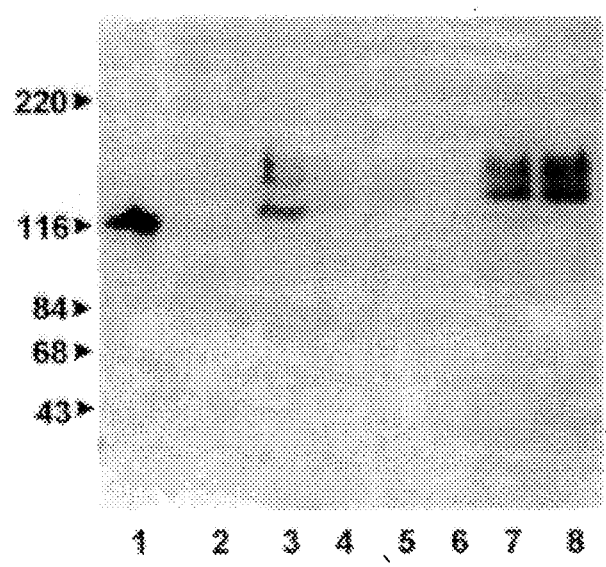
FIG. 1. Immunoblot analysis of fusion proteins from the λASGP2 clones. Phage clones were used to infect E. coli and prepare the fusion proteins as described in the EXAMPLES. The fusion proteins were fractionated by SDS PAGE (8%), transferred to nitrocellulose, and incubated with anti-β-galactosidase (lane 1) and anti-ASGP-2 (lanes 2–8). Lysate of E. coli infected with: lanes 1 and 2, λgt 11 phage; lane 3, λASGP2.4-1; lane 4, λASGP2.4-4; lane 5, λASGP2.1-4; lane 6, λASGP2.6-2; lane 7, λASGP2.6-3; lane 8, λASGP2.9-1.

As indicated above, the cell surface sialomucin complex of 13762 rat mammary adenocarcinoma cells is composed of the sialomucin ASGP-1 and the membrane-associated, N-glycosylated glycoprotein ASGP-2 (Sherblom and Carraway (1980) J. Biol. Chem. 255:12051–12059). These are synthesized as a high $M_r$ precursor pSMC-1, which is cleaved early in the transit to the cell surface. The present invention resulted, at least in part, from the isolation of cDNA clones encoding ASGP-2 from expression libraries made with mRNA from 13762 rat mammary adenocarcinoma cells.

Accordingly, in one embodiment, the present invention relates to a DNA segment encoding the transmembrane component of a cell surface sialomucin complex, preferably, a sialomucin complex present on the surface of tumor cells, for example, carcinoma cells, including adenocarcinoma cells, such as mammary adenocarcinoma cells. In a specific embodiment, the DNA segment encodes ASGP-2, or portion thereof at least 10, preferably, at least 50, more preferably, at least 100, and most preferably, at least 250 amino acids in length. The DNA segment can be purified from natural sources, reverse transcribed from mRNA or chemically synthesized, any of which procedures can be carried out using methods known in the art.

In another embodiment, the present invention relates to a recombinant DNA molecule comprising the above-described DNA segment (or portion thereof) and a vector. The vector can take the form of a virus (for example, λgt11, λZAP, λgt10 (procaryotic); Moloney MXV (animal); baculovirus (insect)), or a plasmid (for example, pcDNAII, pIN, Bluescript M13 (procaryotic); pSV2, pcDNAI (animal); pGPD-2 (yeast)). The DNA sequence can be present in the vector operably linked to regulatory elements, including, for example, a promoter. The recombinant molecule is suitable for transforming procaryotic or eucaryotic cells, advantageously, mammalian cells.

In a further embodiment, the present invention relates to a host cell comprising the above-described recombinant molecule. The host can be procaryotic (for example, bacterial), lower eucaryotic (e.g., fungal, including yeast) or higher eucaryotic (e.g., mammalian, including human). Introduction of the recombinant molecule into the host cell can be effective using methods known in the art. The host cells comprising the recombinant molecule can be used as a source for the DNA segment described above (which segment constitutes part of the recombinant molecule). When the recombinant molecule takes the form of an expression system, the host cells containing same can be used as a source of the protein encoded in the segment.

In another embodiment, the present invention relates to the transmembrane protein itself. Preferably, the protein is produced by growing the above-identified host cells under conditions such that the DNA segment is expressed. It will be clear to one skilled in the art that the amount and/or pattern of glycosylation of the resulting protein product will vary depending on the host cell used. In a preferred aspect of this embodiment, the protein is present in purified form, for example, free of proteins with which it is naturally associated, with the exception, where appropriate, of protein with which it is naturally complexed (e.g., ASGP-1).

As will be clear from the Examples that follow, the transmembrane protein to which the invention relates (as exemplified by ASGP-2) is characterized by the presence of two EGF-like domains. While other proteins contain regions of homology to EGF, with cysteine residues at similar positions (Davis (1990) New Biologist 2:410–419), few have been demonstrated to have EGF-like activities. Sequence comparisons of the EGF-like domains of ASGP-2, however, indicate substantial identities with the consensus residues for active members of the EGF family (FIG. 6). In contrast, proteins that contain EGF-like domains, but exhibit no activity, are missing some or all of these consensus residues (FIG. 4).

Sequence comparisons of ASGP-2 and heregulin/NDF/ARIA/GGF, which will activate p185, reveal that the only common regions are the EGF-like domains (FIG. 17). ASGP-2 has two of these, EGF1 and EGF2. Sequence alignments indicate that they are substantially different in structure. As shown in FIG. 17, EGF1 and EGF2 have been compared by aligning their sequences with the six cysteine residues which are believed to form disulfide loops comparable to those found in EGF and its analogs. One uncertainty in this alignment is that both EGF1 and EGF2 of ASGP-2 contain more than six cysteine residues. EGF1 has eight, which provides the potential for forming a fourth disulfide loop. EGF2 has seven in the sequence shown, but also has another cysteine 18 residues toward the N-terminus, which may be involved in formation of another loop. EGF1 and EGF2 also differ in the sizes of two of the disulfide loops, loops 2 and 3 according to the convention used with the EGF family. ASGP-2 EGF1 has 17/35 identical residues from C1 to C6 when aligned with EGF2. By contrast, rate EGF has only 13/37 identical residues when similarly aligned with rat TGFα. These comparisons of EGF1 and EGF2 with heregulin/NDF/ARIA/GGF show some interesting contrasts. Both of the ASGP-2 combines differ in loop structure from heregulin. In addition to having the potential for forming four-loop structures, both ASGP-2 domains have smaller loop 1 and loop 2 structures than the heregulin analogs. In addition, EGF2 has a larger loop 3. ASGP-2 EGF1 has 13/35 and EGF2 has 18/36 residue identities with the heregulin analogs.

Figure 8:
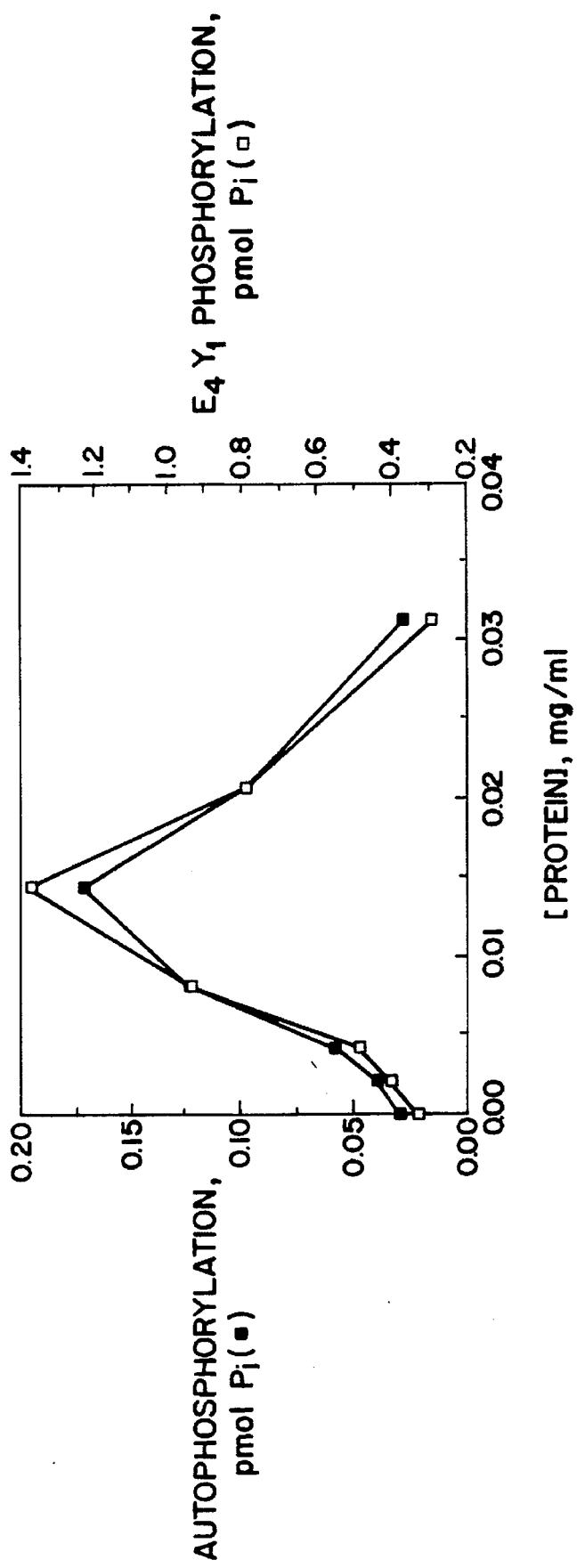
FIG. 8. Modulation of EGF receptor kinase by purified ASGP-2. Plasma membranes from A431 cells (containing 5 nM [$^{125}$I]EGF binding sites) were incubated in the presence of increasing concentrations of ASGP-2. The reactions were then incubated with poly(glu$_4$tyr) and phosphorylated with [gamma-$^{32}$P]ATP. Phosphorylated products were detected by SDS-PAGE and autoradiography. Quantitative measurements were made by excising the radioactive bands and counting.

When ASGP-2 is incubated with A431 cell membranes, which are enriched in the EGF receptor, a biphasic modulation of receptor phosphorylation is noted (see FIG. 8). These results indicate that ASGP-2 is a transmembrane growth factor.

Sheng et al ((1992) J. Biol. Chem. 267, 16341–16346), published after the filing of the parent application (U.S. Ser. No. 07/922,521), hypothesized that because a modulation of EGF receptor phosphorylation is noted when A431 cell membranes were incubated with ASGP-2, ASGP-2 may be a transmembrane growth factor. It was also proposed that ASGP-2 binds to a receptor in the 13762 cell membranes to maintain the cells in a constantly stimulated state which could, potentially, provide a mechanism for autonomous growth stimulation for the tumor cell. The authors concluded that the findings presented in Sheng et al indicate that the sialomucin complex was bifunctional, possessing both anti-recognition and growth regulatory activities. Sheng et al did not present or suggest the relationship between ASGP-2 and p185 or any other oncogene product, as disclosed in the parent or present application. Sheng et al does present the comparison between segments of ASGP-2 and known EGF-like domains.

Two observations suggest that the EGF receptor is not the direct target for the present membrane ligand however. First, the affinity of the ligand for the EGF receptor is not very high. Second, immunoblot analyses found no EHGF receptor present in membranes from the 13762 cells (Carraway et al, 1993). These observations suggest that ASGP-2 might serve as a ligand for a different receptor which is similar to the EGF receptor.

The data presented in Example 7 below indicate that the transmembrane protein to which the invention relates, as exemplified by ASGP-2, acts as a ligand for p185$^{neu}$, the product of the growth-related neu oncogene. Two other ligands for p185 have recently been described (Wen et al, Cell 69:559–572 (1992); Holmes et al, Science 256:1205–1210 (1992)), but ASGP-2 is clearly different from both of them. The human counterpart to neu, c-erbB-2, is found in high levels in certain human malignancies, but not in their normal tissue counterparts. The presence of c-erbB-2 is noted in 20–30% of breast cancers and indicates a poor prognosis for the cancer patient.

Figure 18A:
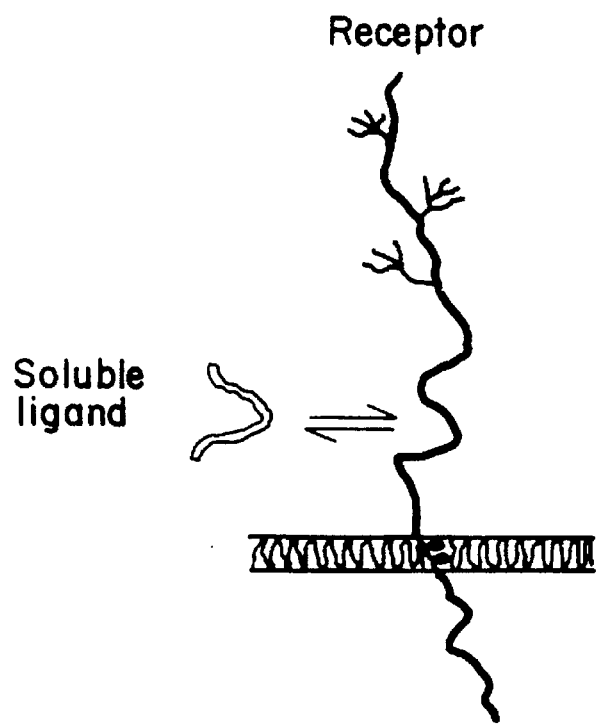
FIG. 18A and 18B. Intramembrane model for association and activation of p185$^{neu}$ by ASGP-2.
Figure 18B:
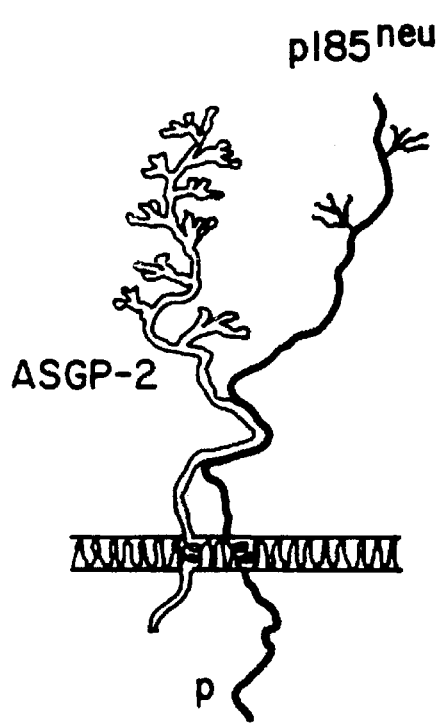
Figure 19:
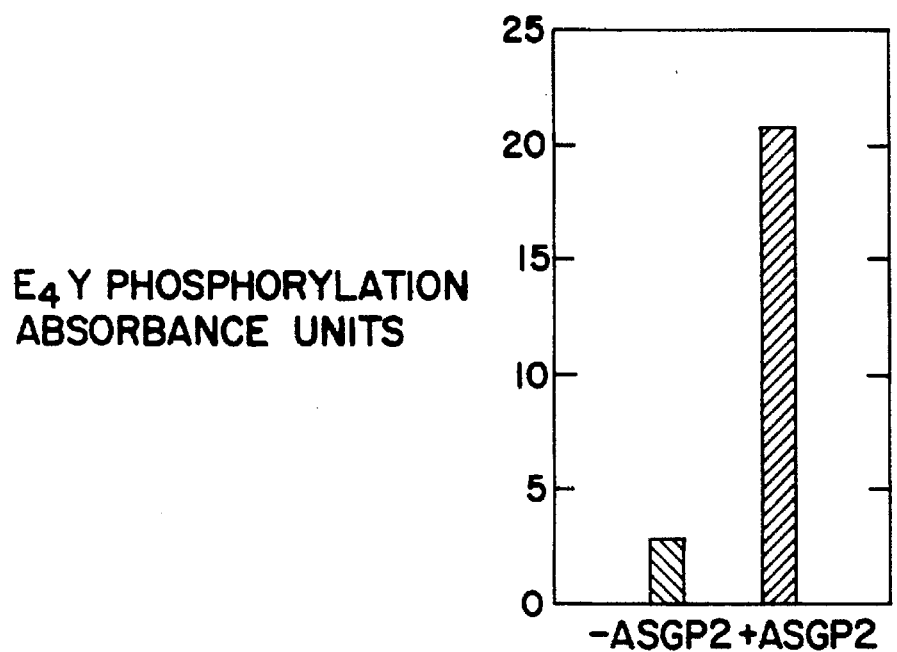
FIG. 19. Stimulation of tyrosine kinase of 3T3 DHFR/G8 membranes by ASGP-2. Membranes from 3T3 DHFR/G8 cells were incubated with ASGP-2 as described in Examples and with $E_4Y$ as exogenous substrate for 10 min. Phosphorylation was initiated with the addition of $MgCl_2$ to 10 mM and [gamma-$^{32}$P]ATP to 6 µM. After 5 min the reactions were stopped with electrophoresis sample buffer, proteins were resolved by SDS PAGE, and phosphorylated proteins were detected by autoradiography. For quantitation, the autoradiograms were analyzed by densitometry.

The results presented in the Examples, below, detail the applicants' discovery that ASGP-2 will stimulate autophosphorylation of p185$^{neu}$ from cells transfected with c-neu. Moreover, ASGP-2 has been discovered to be present as a complex with p185 in the 13762 cell membranes and it is suggested that the complex of ASGP-2 and p185$^{neu}$ provides an autonomous growth mechanism for metastatic tumor cells, and that, ASGP-2 and p185 form a cell surface integral membrane complex by an intramembrane mechanism, as shown in FIGS. 18A and 18B. These results raised the question whether ASGP-2 and p185 associate to form an active complex.

Several lines of evidence support this hypothesis. 1) Treatment of 3T3 DHFR/G8 membranes from cells transfected with c-neu with purified ASGP-2 results in the activation of p185 autophosphorylation. 2) The p185 is the only tyrosine-phosphorylated product detected in the receptor $M_r$ range in the ASGP-2-treated membranes. 3) ASGP-2 and p185 co-immunoprecipitate from detergent lysates of the treated membranes, even in the presence of RIPA buffer, which is routinely used for dissociation of membrane complexes. 4) ASGP-2 and p185 can also be co-immunoprecipitated from detergent extracts of 13762 ascites cell membranes after density gradient fractionation of the extracts to separate soluble and insoluble complexes. 5) ASGP-2 and p185 can be co-immunoprecipitated from both crosslinked and uncrosslinked ascites cell microvilli after solubilization in SDS and reconstitution into RIPA buffer. These results indicate that the ASGP-2 and p185 readily reassociate into a complex, even after denaturation. Undoubtedly, renaturation and complex formation are aided by the fact that both the extracellular domain of the EGF receptor and the EGF-like domains are stabilized by intramolecular disulfides. Proteolytic release of ASGP-2 fragments is unlikely to contribute to this complex formation. First, the ASGP-2 found in complexes with p185 and the 13762 cells is indistinguishable in size from ASGP-2 directly solubilized from cells or microvilli. Second, a released fragment of ASGP-2 would have to compete with the membrane form, which has an extremely high effective concentration because of the intramembrane effect mentioned above, and the large amount of ASGP-1/ASGP-2 complex (approx. $10^6$ molecules per cell) present on these cells. Thus, the p185 should be saturated with membrane ASGP-2 ligand. This high amount of sialomucin complex has been shown to provide protection for the ascites cells against destruction by cells of the immune system (Sherblom and Moody, 1986). The high negative charge provided by the sialomucin also prevents cell-cell interactions of the ascites cells. Thus, an intercellular or juxtacrine mechanism for the interaction of the ASGP-2 and p185 is highly unlikely. All of these results are consistent with an autonomous growth mechanism for the ascites cells via a direct intramembrane complex of ASGP-2 and p185.

Previous studies from several laboratories have identified an activator of p185 from several sources and species, variously called heregulin, NDF, ARIA, and GGF (Wen et al, 1992; Holmes et al, 1992; Falls et al, 1993; Marchionni et al, 1993). However, this protein is unable to bind p185-containing cells or stimulate p185 autophosphorylation in a number of systems, including the 3T3 DHFR/G8 membranes treated under conditions similar to those described here for ASGP-2. These results indicate that both ASGP-2 and the heregulin can activate p185, but that the activations involve somewhat different mechanisms. Peles et al (1993) have suggested that a second cellular component is involved in the activation of p185 by NDF/heregulin. The applicants' results with the 3T3 DHFR/G8 membranes indicate that this component is not required for the activation of p185 by ASGP-2.

Accordingly, the present invention further relates to methods and reagents useful in these methods for identification and, separately, elimination of cells containing receptors which bind the ligand of the present invention. One skilled in the art will appreciate that the ligand may be modified chemically or recombinantly to include quantifiable labels, radioisotopes or toxins useful in these methods without departing from the scope of the instant invention. The ability of ASGP-2 to bind with receptors specifically found at high levels on certain types of tumor cells provides a method to identify these cells using radioligand methodologies known to one skilled in the art, such as, for example, imaging by radio-scintigraphy. Further, the binding of ASGP-2 to its receptor may be exploited to chemically or recombinantly modify the ligand by methods known in the art to produce ligand-toxin conjugates useful in methods to eliminate cells containing the receptor for the ligand. One skilled in the art will appreciate that radioactive isotopes may be used in place of toxins to kill cells targeted for by the ligand of the invention.

The availability of the transmembrane protein encoding DNA to which the invention relates makes possible the production of large quantities of the protein itself using recombinant DNA technology. Likewise, modified forms of the protein can be engineered. For example, a chimeric molecule containing an EGF-like domain of ASGP-2 and a cell toxin can be produced, in the manner known by those skilled in the art, such as, for example, that described by Pai et al (Cancer Research (1991) 51:2808–2812). Alternatively, an EGF-like domain from ASGP-2 can be chemically coupled to a toxin or anti-cancer drug. The availability of these proteins can be expected to result in the development of specific therapies for cancers that over express the neu proto-oncogene. For example, modified forms of the protein can be expected to serve directly as antagonists of $p185^{neu}$. In addition, as discussed above, forms of the protein can be engineered to carry toxins, anti-cancer drugs or radioisotopes specifically to the neu-expressing cells.

In tumors, particularly human tumors, in which ASGP-2 is expressed, antibodies against ASGP-2 can be used for diagnosis and prognosis. Such antibodies can be monoclonal or polyclonal and can be produced using methods known in the art. Binding fragments of such antibodies can also be used. Further, the protein is expected to be useful as a stimulating agent in tissues containing the receptor, such as, for example, in spinal chord regeneration. One skilled in the art will appreciate that neural cell and spinal chord regeneration will entail methods of using the ligand of the instant invention which are distinct from the methods of tumor therapy, such as, for example, in the expected modes of administration of therapeutic compositions containing the present invention.

Certain embodiments of the present invention are described in further detail by reference to the following non-limiting Examples.

EXAMPLES

The following protocols and experimental details are referenced in the specific Examples that follow:
Construction of the cDNA libraries:

Ascites cells of the MAT-C1 subline of the 13762 rat mammary adenocarcinoma were used for the preparation of RNA by the guanidinium thiocyanate method (Chirgwin et al (1979) Biochemistry 18:5294). Poly (A)$^+$RNA was prepared and used to synthesize double-stranded cDNA using kits from BRL or Invitrogen, according to the manufacturer's recommendations. Size-fractionated, double-stranded cDNAs were cloned into either λgt11 after blunt ending and addition of Eco RI linker DNAs, or into pcDNAII plasmid using the directional Librarian system (Invitrogen, Inc.). cDNAs ligated to phage DNAs were packaged in vitro using packaging extracts (Stratagene) according to the manufacturer's recommendation, and cDNAs ligated into the plasmid vector were transformed into *E. coli* by electroporation.

Immunological Screening:

Antiserum or blot-purified antibody to ASGP-2 (Sheng et al (1990) J. Biol. Chem. 265:8505–8510) was incubated several times with the nitrocellulose filters saturated with lysates from *E. coli* Y1090 infected with λgt11 phage. Filters to be screened were blocked with 3% BSA before incubation with antibody (Young et al (1983) Science 222:778–782). Antibody-binding clones were identified using an alkaline phosphatase-conjugated second antibody. First round screening was done on 150 mm plates with $5 \times 10^4$ bacteriophage per plate. Positive plaques were isolated and further purified by repeated antibody screening.

Analysis for Fusion Proteins:

Lysogenization of *E. coli* Y1090 with phage and induction of fusion proteins with isopropyl β-D-thiogalactoside were performed as previously described (Young et al (1983) Science 222:778–782). The lysate was analyzed for fusion proteins by SDS PAGE and immunoblotting using anti-ASGP-2 (Sheng et al (1990) J. Biol. Chem. 265:8505–8510).

DNA Sequence Analysis:

The insert from the λASGP2.9-1 was subcloned into the EcoRI site of pGEM-3Z (Promega) and was sequenced by the dideoxynucleotide chain termination method on double-stranded DNA, using primers complementary to the SP6 promoter and the T7 promoter sequence and T7 DNA polymerase (SEQUENASE, United States Biochemical Corp.). Several subclones were constructed using restriction enzyme sites discovered in the initial sequencings and sequenced similarly. In some cases, oligonucleotides complementary to the sequences determined from previous experiments were synthesized and used as primers for further sequencing reactions.

RNA Gel Blotting:

Total RNA and poly (A)$^+$RNA from 13762 rat mammary tumor ascites cells were electrophoresed in 1% agarose/formaldehyde gels and blotted to nitrocellulose overnight with 20×SSC (1×SSC=0.15M NaCl, 0.015M NaCitrate, pH 7.0). The filters were rinsed with 20×SSC and baked for 2 hours at 80° C. in a vacuum oven. The blots were hybridized at 42° C. in 50% deionized formaldehyde, 0.6M NaCl, 75 mM sodium citrate, 65 mM NaH$_2$PO$_4$, 5 mM EDTA, 1× Denhardt's solution (0.02% each Ficoll, polyvinyl pyrolidone and BSA) and 0.2% SDS, pH 7.2, with $10^6$ cpm/ml probe. The probe was the entire 1.3 kb EcoR1 insert fragment which was isolated from λASGP2.9-1 by agarose gel electrophoresis and labeled with $^{32}$p by nick translation (Maniatis et al (1982) Molecular Cloning, Cold Spring Harbor, New York). Blots were washed after hybridization with 4×SSC, 0.1% SDS, followed by two 15 min washes in 2×SSC, 0.1% SDS, and a 15 min wash in 0.2×SSC, 0.1% SDS at 55° C. Autoradiography was performed for 1 day at −70° C. with an intensifying screen.

Peptide preparation and sequencing:

The N-terminal amino acid sequence of purified ASGP-2 (Hull et al (1990) Biochem. J. 265:121–129) was determined by gas phase sequencing (Hunkapiller et al, Meth. Enzymol. 91:399–413 (1983)). For preparation of cyanogen bromide peptides of ASGP-2, sialomucin complex was purified by CsCl density gradient centrifugation as described by Hull et al ((1990) Biochem. J. 265:121–129). The complex was then dialyzed against 10 mM Tris, pH 8.0, 0.05% SDS and concentrated. The ASGP-2 was purified by preparative SDS PAGE and electroelution. About 200 μg of gel-purified ASGP-2 was lyophilized and resuspended in 0.5 ml CNBr/formic acid solution (20 mg CNBr dissolved in 1 ml 70% formic acid, prepared fresh), and kept at room temperature for 24 h in the dark. The reaction mixture was diluted with 5 ml of H$_2$O and lyophilized. The CNBr cleavage products were fractionated by SDS PAGE, and a 6 kDa peptide was isolated by electro-transfer to Immobilon-P (Millipore Corp.) and sequenced (Hunkapiller et al (1983) Meth. Enzymol. 91:399–43).

Cells, microvilli and membranes:

Ascites 13762 adenocarcinoma cells (MAT-C1 subline) were grown in Fischer 344 rats (Carraway et al, 1979). Microvilli were sheared from these cells using a 14 gauge syringe needle and isolated by centrifugation (Carraway et al, 1980; Carraway et al, 1982a). Microvillar membranes were prepared under microfilament-depolymerizing conditions (Carraway et al, 1982ab). For the membrane preparation microvilli (5.0 ml, ≈15 mg/ml protein) were incubated for 30 min at 4° C. in 5 mM glycine, 2 mM EDTA, 2 mM dithiothreitol, pH 9.5, and homogenized in a Dounce B homogenizer. After centrifugation at 10,000 g the membranes were harvested and washed at 150,000 g for 1.5 hr.

DHFR/G8 cells were cultured in DMEM 1965 medium (GIBCO/BRL) supplemented with 10% calf serum (GIBCO/BRL), 100 U/ml penicillin G and 100 μg/ml streptomycin at 37° C. and 5% CO$_2$ in a humidified incubator. Confluent cultures in 100 cm$^2$ petri dishes were passaged by a 5 min incubation in a 1 ml trypsin/EDTA solution (GIBCO/BRL). Media was aspirated from 30 confluent dishes which were then washed with 5 ml Hanks solution for 10 minutes at room temperature. The cells were scraped off the dishes and pelleted at 1500 g. The pellet was resuspended in HEPES-PI (20 mM HEPES pH 7.4, 1 mM PMSF, 0.1 mM pepstatin, 1 mM benzamidine, and 20 KIU/ml aprotinin), then incubated on ice for 15 minutes and homogenized (15 strokes) in Dounce B homogenizer. The homogenate was centrifuged at 1500 g for 10 minutes at 4° C. and the supernate was transferred to Eppendorf tubes. Membranes were pelleted at 15,000 g for 15 minutes at 4° C. The membranes were resuspended in HEPES-PI and pelleted again. The membranes were stored in HEPES-PI with 50% glycerol at −20° C.

Phosphorylation of p185 in DHFR/G8 membranes:

DHFR/G8 membranes (15 μl) were washed once with 1 ml of buffer A (10 mM Hepes, pH 7.4, 20 mM MgCl$_2$, 100 μM leupeptin, 20 KIU/ml aprotinin, 1 mM PMSF, 1 mM benzamidine) and centrifuged at 15,000 g and 4° C. for 15 minutes. The membranes were resuspended in 40 μl Buffer A, and ASGP-2 or EGF in buffer A containing 0.02% Triton X-100 was added and incubated for 2 hours at room temperature. The membranes were phosphorylated by the addition of 5 μCi/reaction of gamma-$^{32}$P-ATP in a final volume of 50 μl. After 10 minutes at room temperature, samples were solubilized in RIPA buffer (150 mM NaCl, 1% NP-40, 0.5% deoxycholate, 0.1% SDS, 50 mM Tris, pH 8.0) for immunoprecipitation or prepared for SDS PAGE.

Immunoprecipitation:

DHFR/G8 membranes treated with ASGP-2 were solubilized in RIPA buffer or 0.5% Triton X-100 buffer for 15 minutes at room temperature. Antibodies for p185 (Ab-3 from Oncogene Science, 60 μl) or anti-ASGP-2 (100 μl) were preincubated with equal amounts of Protein A-Sepharose for one hour, added to the Triton extract and rotated at 4° C. for two days. Immunoprecipitates were centrifuged at 1000 g, washed twice with PBS, resuspended in 50 μl of electrophoresis buffer and analyzed by SDS PAGE and immunoblotting. Microvilli (40 μl) were solubilized in 0.5% SDS buffer for 15 minutes at room temperature. The SDS was displaced by either 3% Triton X-100 or RIPA buffer without SDS (150 mM NaCl, 1% NP-40, 0.5% deoxycholate, 50 mM Tris (8.0). The final concentration of SDS was 0.1%. After 1–4 hours incubation the samples were immunoprecipitated with either anti-p185, mouse nonimmune (15 µl), anti-ASGP-2 or rabbit preimmune (20 µl) as described above.

Western blotting:

Electrophoresis buffer (50 µl) was added to samples, which were boiled for 5 minutes before loading onto an 8% acrylamide gel. Gels were either stained with Coomassie Blue or transferred onto nitrocellulose (anti-p185 and anti-ASGP2) (Carraway et al, 1993; Vanderpuye et al, 1989) or Immobilin-P (anti-pTyr) using the Biorad rapid blot system. Anti-p185 blots were blocked in 0.5% milk/TTBS (0.05% Tween 20, 500 mM NaCl, 50 mM Tris, pH 8.0) for one hour and incubated with anti-p185 (Ab-3, Oncogene Science) in 0.5% milk/TTBS (1:300) for 3 hours. Anti-p185 Ig was detected with Sigma rabbit-anti-mouse alkaline phosphatase-conjugated second antibody (1:4000). Anti-ASGP-2 blots were blocked in 3% bovine serum albumin/TTBS for one hour and incubated in anti-ASGP-2 (1:1000) in 0.3% BSA/TTBS for two hours. Antibody complexes were detected with Biorad goat anti-rabbit alkaline phosphatase-conjugated second antibody. Anti-pTyr blots were blocked in 3% BSA/TTBS for one hour and incubated with anti-pTyr in 0.3% BSA/TTBS (1:1000) for two hours. The antibody complexes were detected with Biorad goat-anti-rabbit alkaline phosphatase conjugate (1:4000). Con A blots were performed as previously described (Carraway et al, 1993).

Sucrose density gradient centrifugation:

Extracts of microvillar membranes were centrifuged on 7–25 % sucrose gradients in buffer for 15 hours at 80,000 g and 4° C. (Carraway et al, 1983a). Fractions were extracted from the top of the tube and prepared for SDS PAGE. Selected fractions were combined, phosphorylated and analyzed by immunoprecipitation.

Crosslinking:

Microvilli (1.5 mg protein) were incubated with 1.0 mM DTSSP in 25 mM Hepes, pH 7.4, in a total volume of 400 µl. After 30 minutes the reaction was quenched by the addition of 100 µl each of 20 mM NEM, 50 mM ethanolamine, and 50 mM Tris-Cl, pH 7.4. The crosslinked microvilli were solubilized with 0.2% SDS for 15 minutes in the presence of protease inhibitors. An equal volume of 2× RIPA minus SDS (300 mM NaCl, 2% NP-40, 1% deoxycholate, 100 mM Tris-Cl, pH 8.0) was added and incubated for 30 minutes at room temperature. Samples were immunoprecipitated with 60 µl anti-p185$^{neu}$ (antibody-3 from Oncogene Science) that had been preincubated with protein A-Sepharose. Immunoprecipitation reactions were rotated at 4° C. for two days, washed twice with PBS, pelleted and resuspended in 50 µl sample buffer for analysis by SDS PAGE and immunoblotting.

EXAMPLE 1

Screening of MAT-C1 cDNA Libraries

The λgt11 cDNA expression library was screened using an anti-ASGP-2 antibody as described above. Screening 4×10$^5$ phage gave nine positive clones after 4 rounds of plaque purification. Restriction enzyme analysis of the insert DNA from the strongest antibody-binding clone, λASGP-2.9-1, showed a 1.3 kb insert fragment which was also seen in several of the other positive clones. Southern blot hybridizations using the 1.3 kb fragment as a probe showed that the 1.3 kb fragment cross-hybridized with the other inserts, indicating that these were all derived from the same mRNA.

β-Galactosidase fusion proteins were prepared from *E. coli* lysogenized with the plaque-purified phage, and analyzed by SDS PAGE and immunoblotting with anti-ASGP-2 (FIG. 1). Antibody-reactive proteins were only observed in lysates from the cDNA insert phage lysogens, and not from lysogens containing only λgt11 vector. The reacting proteins were smaller than β-galactosidase, indicating the presence of a translation terminator in the insert.

EXAMPLE 2

Sequence of the ASGP-2 Inserts

The 1.3 kb EcoR1 fragment from λASGP-2.9-1 was subcloned into pGEM-3Z and sequenced by dideoxynucleotide chain termination techniques. The sequencing strategy involved the generation of deletions from the insert ranging from 200–500 bases, using restriction endonuclease sites discovered by earlier sequencing experiments. An oligonucleotide containing a sequence complementary to the 5' end of the λASGP-2.9-1 insert was synthesized and used to screen colonies from another library constructed by directional cloning of 13762 MAT-C1 cDNAs into pcDNA II. This screen resulted in the identification of several more ASGP-2 clones including one clone, pASGP-1/2.1, which contained a 5.4 kb insert. The insert of this clone was partially sequenced and found to contain the same 3' sequence as λASGP-2.9-1, plus additional 5' sequence, presumably extending into the ASGP-1 coding domain. Sequencing was performed by a sequential procedure using oligonucleotide primers complementary to sequences from the most 5' regions of earlier sequencing reactions as well as by construction of sub-clones.

Analysis of approximately 2600 nucleotides of the 3' end of pASGP-1/2.1 insert (including the entire λASGP-2.9-1 insert) revealed an open reading frame of 2190 bps encoding a protein of 744 amino acid residues with a calculated molecular mass of about 81 kDa (FIGS. 2A–2I). Within this open reading frame two peptide sequences were identified which were identical to two amino acid sequences obtained by protein sequencing of ASGP-2. These included a 12 amino acid sequence from the amino terminus of ASGP-2, X-X-I-T-T-L-D-N-A-K-Y-T-F-N(X, indeterminate residue; SEQ ID N0:93; amino acids 17–30, FIG. 2–2I), and a 19 amino acid sequence, M-R-A-F-L-S-N-S-L-V-E-L-I-R-T-S-P-G-A (amino acids 535–551, SEQ ID NO:94; FIG. 2), obtained from a 6 kDa CNBr fragment of ASGP-2. Amino acid sequence analysis of the N-terminus of ASGP-2 was unable to identify the first two amino acids in the protein. The cDNA sequence found these to be proline and histidine, and suggested that the processing of pSMC-1 into ASGP-1 and ASGP-2 involves the cleavage between the aspartic acid and proline (amino acids 16 and 17 in FIGS. 2A–2I). The open reading frame continues to the 5' direction, presumably into the ASGP-1 coding region. The coding sequence is followed by a 3' untranslated region of 355 nucleotides, including several potential polyadenylation signals, AATAAA, ATTAAA and TATAAA. Thus, the protein sequence deduced from cDNA clone represents the carboxyl terminus of the protein, pSMC-1. The deduced amino acid sequence of ASGP-2 is shown in FIG. 2 along with the 15 amino acids preceding the N-terminus to define the cleavage site for the production of ASGP-2 from pSMC-1.

Figure 3:
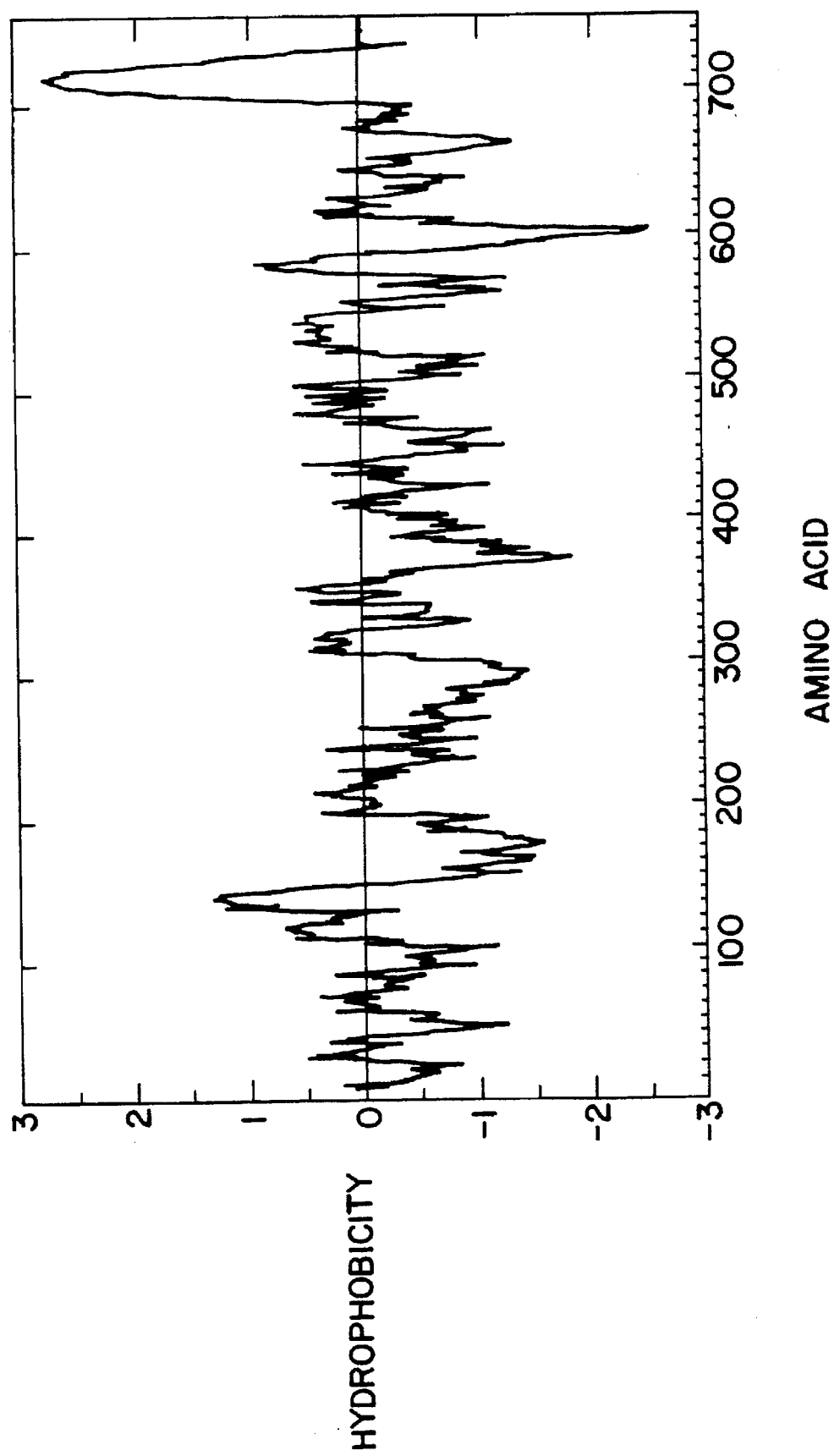
FIG. 3. Hydropathy plot of ASGP-2. Computer-generated plot of the hydrophobicity by the method of Kyte and Doolittle, 1982 (J. Mol. Biol. 157:105), using a window size of 17 amino acids. Regions above the horizontal axis are relatively hydrophobic, whereas regions below the horizontal axis are hydrophilic.

The hydropathy profile of the primary structure of ASGP-2 was obtained by computer analysis (Kyte et al (1982) J. Mol. Biol. 157:105–132) and revealed a single hydrophobic region of about 26 hydrophobic amino acids (amino acids 660–694, FIGS. 2A–2I), which represents a potential membrane spanning domain (FIG. 3). Thus, the C-terminus of ASGP-2 contains the putative transmembrane region. Since most of the sialomucin is readily cleaved by protease from the cell surface (Sheng et al (1990) J. Biol. Chem. 265:8505–8510) and the cDNA coding for the putative transmembrane region is close to the 3' untranslated region (corresponding to carboxyl-terminal of protein), the protein must be oriented with its N-terminus extracellularly. The putative intracellular region at the C-terminus of the protein is only about 20 amino residues in length. Examination of the amino acid sequence for potential N-glycosylation sites (tripeptides NXT and NXS) revealed 24 of these tripeptides, all of which are within the predicted extracellular domain. Recent studies have suggested that the sialomucin complex is endocytosed and rapidly recycled through the cell (Hull et al (1991) J. Biol. Chem. 266:13580–13586). Receptor-mediated recycling requires an exposed tyrosine in the cytoplasmic domain of the cell surface component (Ktistakis et al (1990) J. Cell Biol. 111:1393–1407). Amino acid residue 738 within the cytoplasmic domain is a tyrosine and could satisfy that requirement for receptor-mediated recycling.

The derived amino acid sequence was used to search the protein sequence database of the National Biomedical Research Foundation for homologous proteins using the program FASTDB (Intelligenetics, Corp.). This search revealed two sequences homologous with a group of proteins with a common EGF-like motif (FIG. 4 shows a selection of these proteins). These proteins include the Drosophila neurogenesis proteins, Notch and Delta, Caenorhabditis lineage factor lin-12, EGF, blood coagulation factors IX, X and protein Z, plasminogen activator, proteoglycan core protein, urokinase, TGF-α, laminin B1 and the LDL receptor. The basis of the homology between ASGP-2 and these proteins is the presence in ASGP-2 of two copies of a cysteine-rich approximately 40 amino acid sequence with an organization similar to that of EGF, termed the EGF-like repeat (Carpenter et al (1990) J. Biol. Chem. 265:7709–7712; Davis (1990) New Biologist 2:410–419). The two ASGP-2 EGF-like repeats were separated by a long stretch (about 160 amino acids) of relatively hydrophilic amino acids, and are 34% homologous with each other. The homology of these repeats to other EGF-like sequences ranges between 20% and 33%, which is about the usual observed range. In general, the EGF-like repeat has six cysteines located at constant positions. The spatial distribution of the cysteine residues follows a pattern consistent with the general formula: $CX_4CX_5CX_8CXCX_8CX$, (SEQ ID NO:95) where C is cysteine and X is any other amino acid. The repeat units are of variable length, but the spacing of the cysteine residues is well conserved in the carboxyl-terminal portion of the repeat, which has the consensus sequence C-X-C-X-X-G-F/Y-X-G-X-X-C (SEQ ID NO:96) (Greenwald (1985) Cell 43:583–590). Other amino acids are also conserved among the related units. Virtually all members share 2 or 3 glycines. Furthermore, the consensus sequence does not identify sites where the substitution of structurally similar amino acids take place, i.e. conservative amino acid substitutions.

EXAMPLE 3

RNA Gel Blot Analysis

Figure 5:
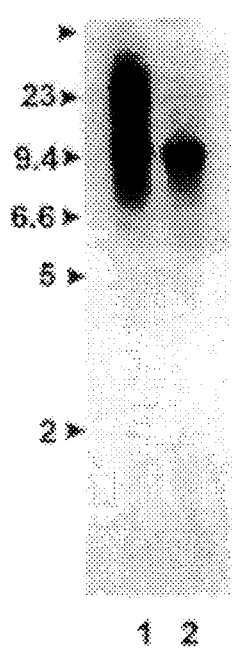
FIG. 5. RNA gel blot analysis of 13762 rat mammary adenocarcinoma ascites cell RNA. 10 µg of total RNA (lane 1) and poly (A)⁺ RNA (lane 2) from 13762 rat mammary adenocarcinoma cells were separated by electrophoresis in 1% agarose-formaldehyde gel in MOPS buffer, transferred, and hybridized with $^{32}$P-labeled 1.3 kb EcoR1 fragment DNA as described in the EXAMPLES.

Previous studies have shown that ASGP-2 is synthesized as part of a larger precursor protein pSMC-1, which has a molecular weight of >250 kDa. Therefore, the λASGP-2.9-1 cDNA insert was derived from a much larger transcript of >7kb. To test this hypothesis, RNA was isolated from 13762 rat mammary tumor ascites cells and examined by RNA gel blot hybridization with $^{32}$P-labeled 1.3 kb λASGP-2.9-1 insert as a probe. The results shown in FIG. 5 indicate that the 1.3 kb insert probe hybridizes to an RNA of approximately 9 kb in length in both total and poly (A)$^+$RNA lanes. The results indicate that this mRNA encodes the entire pSMC-1 precursor protein.

EXAMPLE 4

ASGP-2 is a Ligand for p185$^{neu}$ and the EGF Receptor

To test the functional activity of ASGP-2 as a ligand for EGF receptor kinases, two different preparations were used. In the first case membranes were prepared from cells transfected with c-neu (DHFR/G8 cells) which contain little EGF receptor. In the second case, membranes were prepared from A431 carcinoma cells which have a high content of EGF receptors.

The neu oncogene was first identified by transfection from chemically-induced rat neuroblastomas (Padhy et al, 1982), while its human counterpart c-erbB-2/HER2 was isolated using as a probe the v-erbB gene of avian erythroblastosis virus (Coussens et al, 1985). The structure of the c-erbB-2/neu protein p185 shows significant sequence similarities to the EGF receptor: 40% amino acid identities in the extracellular domain, 82% in the tyrosine kinase domain and similar autophosphorylation sites in the C-terminal region (Gullick, 1990). The most significant difference between the EGF receptor and p185 is that p185 does not bind EGF. Attempts to define a ligand for p185 have led to the isolation and partial characterization of several soluble factors (Yarden and Weinberg, 1989; Lupu et al, 1990; Yarden and Peles, 1991; Davis et al, 1991; Dobashi et al, 1991; Tarakhovsky et al, 1991; Lupu et al, 1992; Wen et al, 1992; Holmes et al, 1992). In four cases cDNAs for these putative, secreted ligands have been isolated and their sequences determined (Wen et al, 1992,; Holmes et al, 1992; Falls et al, 1993; Marchionni et al, 1993). These have been called Neu differentiation factor (NDF), heregulin, acetylcholine receptor inducing activity (ARIA) and glial growth factor (GGF). All four of these exhibit a high degree of amino acid similarity in their EGF-like domains even though they are from different species, indicating that they are derived from the same genes. However, these highly similar gene products, discovered in different cell systems, exhibit strikingly different functional activities. Moreover, recent studies on NDF indicate that it is not active on all cells containing p185 (Peles et al, 1993). These results indicate that the mechanism of action of these factors is more complex than that of EGF. Thus, it was unclear from these results whether another factor was necessary for these EGF-like factors to bind and activate p185, or alternatively, that these ligands act on another receptor, which activates p185.

Figure 7:
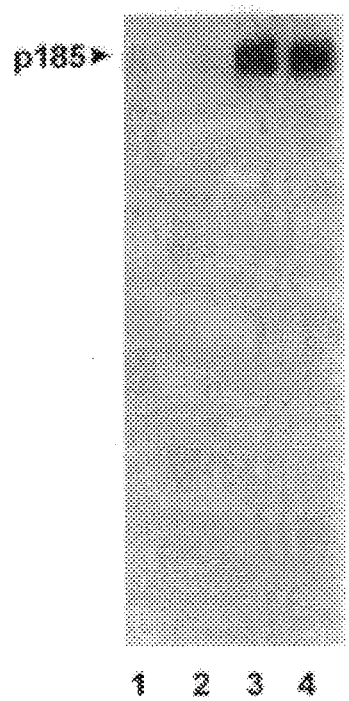
FIG. 7. Autophosphorylation of p185 in the presence of EGF and purified ASGP-2. Membranes from cells transfected with neu were lysed, and lysates were treated with anti-p185 to immunoprecipitate p185. The immunoprecipitates were phosphorylated with $^{32}$P-ATP in the absence of added ligand (lane 1), in the presence of 1 nM EGF (lane 2), in the presence of 0.03 µg/ml ASGP-2 (lane 3) or in the presence of 0.24 µg/ml ASGP-2 (lane 4).

Purified ASGP-2 activated phosphorylation of p185 in DHFR/G8 membranes. To show that this phosphorylation was on p185, the membranes were phosphorylated, and p185 immunoprecipitated under dissociating conditions to remove any bound contaminants (FIG. 7). As a control the effect of EGF on p185 phosphorylated was also examined. EGF did not stimulate phosphorylation of the p185.

For treatments of the DHFR/G8 membranes the purified ASGP-2 was dialyzed into buffer containing 0.02% Triton X-100. EGF was solubilized in the same buffer to use in a control treatment. DHFR/G8 membranes were incubated with both ligands, then phosphorylated with $^{32}$P-ATP. To assess the autophosphorylation of p185, the membranes were solubilized and immunoprecipitated with anti-p185. The immunoprecipitates were analyzed by SDS PAGE and autoradiography. As shown in FIG. 7, essentially no phosphorylation of p185 was observed in the untreated and EGF-treated membranes, but substantial phosphorylation was observed in the ASGP-treated membranes.

Membranes were prepared from A431 carcinoma cells, which have a high content of EGF receptors, as follows. Cells were lysed in pH 10.2 borate solution with vigorous stirring. After centrifugation to remove nuclei, the membranes are partially purified on a sucrose gradient (Carraway et al (1989) J. Biol. Chem. 264:8699–8707). This preparation yields membrane sheets which have been largely stripped of peripheral membrane proteins. The stripping removes non-receptor kinases and phosphatases, simplifying the interpretation of the phosphorylation experiments. Using these membranes, purified ASGP-2 was shown to have a biphasic effect on EGF receptor phosphorylation (FIG. 8). Both enhanced autophosphorylation and phosphorylation of the exogenous substrate poly(glu$_4$tyr) were observed at low concentrations of ASGP-2. However, at higher concentrations, ASGP-2 inhibited phosphorylation. In some experiments this inhibition reduced phosphorylation to levels below that of untreated membranes. These results indicate that ASGP-2 can activate phosphorylation of both the EGF receptor and p185$^{neu}$.

Figures 9A, 9B:
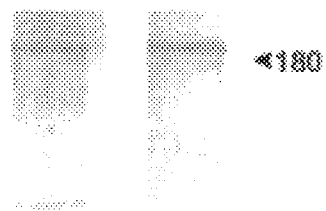
FIG. 9. Tyrosine phosphorylation of DHFR/G98 membranes in the presence of ASGP-2. Membranes were treated with ASGP-2 and phosphorylated as in FIG. 7, but with unlabeled ATP. The phosphorylated membranes were fractionated by SDS PAGE and analyzed by antiphosphotyrosine (lane 1) and anti-185$^{neu}$ (lane 2) immunoblots. Arrowhead denotes position of 180 kDa M, marker.

One mechanism by which p185 can be activated is via the formation of heterodimeric complexes with a second receptor, such as the EGF receptor (Wada et al, 1990). In that case p185 phosphorylation is activated by EGF without binding of ligand to the p185. To determine whether other receptors were phosphorylated in the DHFR/G8 membranes in the presence of ASGP-2, the membranes were phosphorylated as described above with unlabeled ATP and subjected to SDS PAGE and immunoblot analysis with anti-phosphotyrosine (FIG. 9, lane 1) or anti-p185 (FIG. 9, lane 2). The only tyrosine phosphorylated product observed in these membranes in the receptor region was at 185 kDa (FIG. 9). A second tyrosine-phosphorylated product was observed in the 50 kDa region of the gels and may be a substrate for the activated p185.

Figure 10:
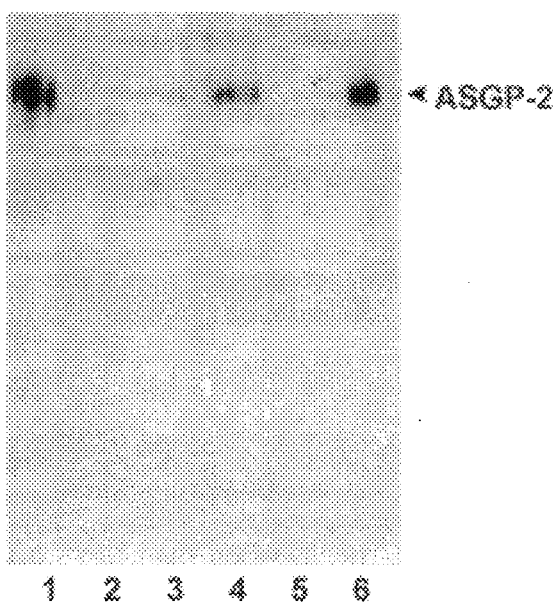
FIG. 10. Co-immunoprecipitation of p185$^{neu}$ and ASGP-2 from 3T3 DHFR/G8 membranes treated with ASGP-2. Membranes were treated with or without ASGP-2 as in FIG. 9, solubilized in 0.5% Triton X-100 or RIPA buffer and immunoprecipitated with anti-p185. The immunoprecipitates were analyzed by SDS PAGE, immunoblotting with anti-ASGP-2 and chemiluminescence detection. Lane 1, microvilli standard; lane 2, ASGP-2-treated membranes solubilized in Triton and precipitated with control class-matched irrelevant antibody; lane 3, untreated membranes solubilized in RIPA buffer and precipitated with anti-p185; lane 4, ASGP-2-treated membranes solubilized in RIPA buffer and precipitated with anti-p185; lane 5, untreated membranes solubilized in Triton buffer and precipitated with anti-p185; lane 6, ASGP-2-treated membranes solubilized in Triton buffer and precipitated with anti-p185.

To test whether ASGP-2 and p185 become associated in a complex in the DHFR/G8 membranes, ASGP-2-treated membranes were phosphorylated with $^{32}$P-ATP, solubilized in Triton-containing buffer and immunoprecipitated with anti-ASGP-2. The immunoprecipitates were analyzed by immunoblot analysis with anti-p185 and autoradiography. As shown in FIG. 10A, p185 is immunoprecipitated with the anti-ASGP-2 in the membranes treated with ASGP-2. Moreover, the autoradiograms indicate that it is phosphorylated by ATP. A small amount of 180 kDa protein staining with anti-p185 also was precipitated in the pre-immune control (FIG. 10A, lane 1). However, the corresponding autoradiogram indicates that it is not phosphorylated and may not be p185.

EXAMPLE 5

Association of ASGP-2 and p185$^{neu}$ in 13762 Cell Membranes

Figures 11A, 11B:
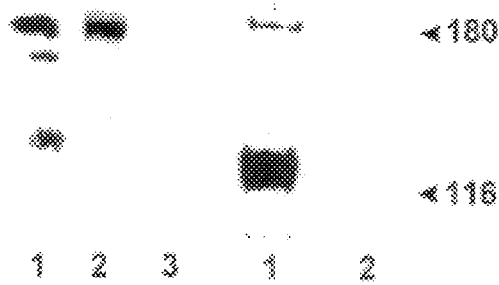
FIG. 11A and B. Co-immunoprecipitation of p185$^{neu}$ and ASGP-2 from extracts of microvillar membranes. Microvillar membranes were extracted with Triton-containing buffer and centrifuged at high speed to remove insoluble complexes. The supernatants were immunoprecipitated with anti-ASGP-2. The immunoprecipitates were analyzed by SDS PAGE and Western blotting with anti-p185 or Con A. Panel A, immunoblot with anti-p185, lane 1, p185 standard from microvillar membranes; lane 2, immunoprecipitate with rabbit anti-ASGP-2; lane 3, immunoprecipitate with pre-immune rabbit serum. Panel B, Western blot with Con A. Lane 1, immunoprecipitate with rabbit anti-ASGP-2; lane 2, immunoprecipitate with pre-immune rabbit serum.

The fact that both ASGP-2 and p185$^{neu}$ are integral membrane proteins suggests that they might form a stable complex in a cell in which both are present. The applicants have previously shown that both ASGP-2 (Sherblom and Carraway, 1980) and p185$^{neu}$ (Carraway et al, 1993) are found in microvilli isolated from 13762 rat mammary adenocarcinoma cells. Moreover, the applicants have shown that a substantial fraction of the p185 is associated with microfilaments and a high M$_r$ glycoprotein complex in these microvilli (Carraway et al, 1993). To examine the association of ASGP-2 and p185 without the complications of the association with microfilaments, microvillar membranes were prepared, which were depleted of microfilaments, and solubilized in Triton X-100. The extracts were centrifuged at high speed to remove insoluble complexes (Carraway et al, 1983ab) and immunoprecipitated with anti-ASGP-2. The immunoprecipitates were analyzed by immunoblotting with p185. As shown in FIG. 11A, p185 was immunoprecipitated with anti-ASGP-2 but not by the control antiserum. Because of problems with immunoblot analyses of immunoprecipitates from these samples, a second type of analysis was required in these studies. Concanavalin A (Con A) blotting was employed as the applicants discovered that Con A binds both p185 and it has been shown that ASGP-2 as well as numerous other cell surface glycoproteins from these microvilli. (Carraway et al, 1991) also bind Con A. As shown in FIG. 11B, p185 and ASGP-2 are the predominant components observed by Con A blotting in the anti-ASGP-2 immunoprecipitates.

Figure 14:
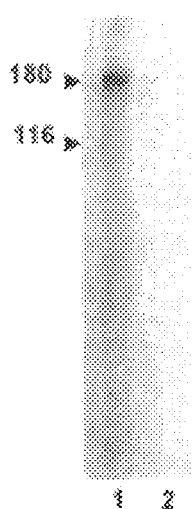
FIG. 14. Phosphorylation of p185 from gradient fractions of Triton-solubilized microvillar membranes. Gradient fractions 10–12 from FIG. 13 were labeled with $^{32}$P-ATP and immunoprecipitated with anti-p185 (lane 1) or mouse non-immune serum (lane 2). The immunoprecipitates were analyzed by SDS PAGE and autoradiography.

As mentioned above, previous studies have shown that p185 is associated with a high molecular transmembrane complex (TMC) (Carraway et al, 1983a) containing a high M$_r$ glycoprotein complex in the microvillar membranes (Carraway et al, 1993). Thus, the co-immunoprecipitation of ASGP-2 and p185 could be due to their common association with a component(s) of this complex. To address that question, density gradient fractionation of Triton-solubilized microvillar membranes was used. This technique has been previously shown to separate populations of p185 which are associated and unassociated with the TMC (Carraway et al, 1993). As shown in FIG. 12B, this technique also fractionates ASGP-2 into populations which are associated or unassociated with the TMC (FIG. 12C). To further assess the association of ASGP-2 and p185, the gradient fractions containing both ASGP-2 and p185 which are not associated with the TMC were examined, that is, those closest to the top of the gradient and of lowest M$_r$. These fractions were labeled with $^{32}$P-ATP and subjected to immunoprecipitation with anti-ASGP-2 and anti-p185. Immunoblots of the immunoprecipitates showed that p185 is precipitated with anti-ASGP-2 (FIG. 13A, lane 2), and ASGP-2 is precipitated with anti-p185 (FIG. 13B, lane 2). Moreover, autoradiograms of SDS PAGE blots of the anti-p185 immunoprecipitates showed a single labeled band at 185 kDa (FIG. 14).

EXAMPLE 6

Crosslinking and Reassociation

Figure 15:
FIG. 15. Crosslinking of microvilli. Microvilli were crosslinked with DTSSP, solubilized in SDS, diluted into RIPA buffer and immunoprecipitated with anti-p185. The immunoprecipitates were analyzed by SDS PAGE and immunoblotting with anti-ASGP-2. Lane 1, microvilli; lane 2, uncrosslinked sample immunoprecipitated with anti-p185; lane 3, crosslinked sample immunoprecipitated with anti-185.

Further evidence of the association of p185 and ASGP-2 was demonstrated using crosslinking studies. For these experiments microvilli were treated with DTSSP, a crosslinking agent which does not readily cross the membrane permeability barrier. Since the microvilli are sealed (Carraway et al, 1983c), crosslinking is limited to the proteins at the exterior surface of the membranes. To detect crosslinked complexes of ASGP-2 and p185, crosslinked and uncrosslinked microvilli were solubilized in SDS to solubilize the microvilli and dissociate the membrane proteins. The extracts were then diluted into RIPA buffer, still containing the SDS, and immunoprecipitated, with anti-p185. The immunoprecipitates were analyzed by immunoblotting with anti-ASGP-2. As shown in FIG. 15, a significant fraction of the ASGP-2 was observed in the anti-p185 immunoprecipitates from the crosslinked, SDS-dissociated sample. Surprisingly, a smaller, but detectable fraction of the ASGP-2 was also observed in the uncrosslinked control. Attempts to observe a crosslinked heterodimeric complex of p185 and ASGP-2 by SDS PAGE were unsuccessful because all of the products detected by immunoblotting with the p185 antibody were >500 kDa. This result is not too surprising, since activated p185 is believed to form a dimer and ASGP-2 is known to be present in the membrane as a complex with ASGP-1 ($M_r$>500 kDa).

Figure 16:
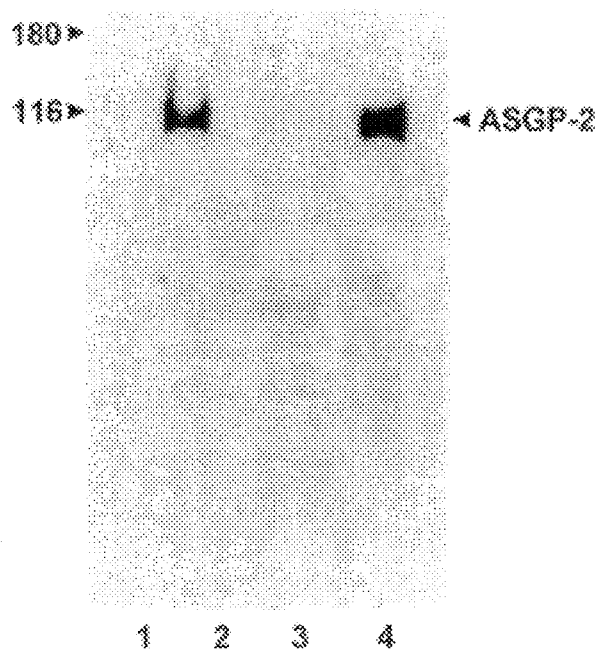
FIG. 16. Reassociation of ASGP-2 and p185. Microvilli were solubilized in SDS, diluted into either RIPA (lanes 1 and 2) or Triton X-100 containing (lanes 3 and 4) buffer and immunoprecipitated with mouse nonimmune serum (lanes 1 and 3) or anti-p185 (lanes 2 and 4). The immunoprecipitates were analyzed by SDS PAGE and immunoblotting with anti-ASGP-2.

The simplest explanation for presence of ASGP-2 in the uncrosslinked anti-p185 immunoprecipitates is that ASGP-2 and p185 are able to reassociate into a complex after dissociation in SDS. Therefore, microvilli were solubilized in SDS under conditions used for dissociation for electrophoresis, then diluted into Triton or deoxycholate/NP-40 buffer, still containing 0.1% SDS for immunoprecipitation with anti-p185. The immunoprecipitates were analyzed by immunoblotting with anti-ASGP-2. ASGP-2 is immunoprecipitated from both buffers by anti-p185 (FIG. 16, lanes 2 and 4), but not by the control nonimmune serum (FIG. 16, lanes 1 and 3). Therefore, the ASGP-2 and p185 are reassociating after dissociation in SDS.

EXAMPLE 7

Absence of ASGP-2 in Ascites Fluid

Most growth factors act in a soluble form. For example, TGF-α is released from the cell surfaces of tumor cells by proteolysis to provide an autonomous mechanism of tumor growth (Massague, 1990). To determine whether ASGP-2 is similarly released, ascites fluid was examined by immunoblot analyses. No evidence was found for a soluble form of ASGP-2 in the ascites fluid.

EXAMPLE 8

Ligands as Carriers

The production of recombinant chimeric toxin-ligands for cancer treatment (Pastan et al, 1991) is known to one skilled in the art. The method is based on the fact that growth factors (ligands) will bind specifically to their receptors which are present at high levels in certain types of tumor cells. For example, the receptor p185$^{neu/HER2}$ for the above-disclosed ligand (ASGP-2) is found in abundance on certain highly malignant breast and ovarian tumors. Therefore, the ligand is expected to preferentially bind to those tumors if infused into the patient. Moreover, ligand bound to receptors on the tumor cells is taken into the cell. If one couples a cell-killing toxin to the ligand, one skilled in the art will expect it to be taken up by the tumor cells. The toxins usually used for these purposes are highly toxic proteins, which act machinery. Since this process is catalytic, one toxin molecule can potentially kill a cell.

The preferred method for making these toxin-ligand conjugates is to use recombinant DNA technology. For example, a chimera has been made of the Pseudomonas exotoxin (PE) and TGF-α, a ligand which binds epidermal growth factor receptor, by coupling a modified toxin gene to the gene of the growth factor (Siegall et al, 1989; Pastan et al, 1989). Since the full length cDNA for ASGP-2 has been isolated, a similar chimeric protein can be made by coupling DNA for the EGF-like regions of the ASGP-2 to PE DNA or other toxins known in the art. The chimeric protein will be expressed and purified as described for the PE-TGFα protein. The primary value of the ASGP-2-PE product is expected to be in treating cancer patients with carcinomas which over-express the receptor p185 on their cell surfaces. These include breast and ovarian cancers which have poor prognoses. The method of delivery of the therapeutic agent is expected to be through intravenous infusion; however, one skilled in the art will appreciate that the mode of administration and treatment regimen may be varied without departing from the scope of the present invention.

Ligands may also potentially be used to deliver chemotherapeutic drugs. However, most of the work in the area of specific drug delivery has utilized monoclonal antibodies (Arnon et al, 1985). One variation of this procedure is to use radioisotopes coupled to antibodies to kill tumor cells (Waldmann, 1991). The advantage of the isotope technique is that the radiation will kill cells other than those to which the antibody or ligand binds. This provides a better opportunity to eliminate all of the tumor, but also may have some deleterious effects on the neighboring normal tissue.

Tumors may be localized for diagnosis and therapy using radioisotopes coupled to binding proteins. Again, essentially all of the work to date has used monoclonal antibodies as the targeting agent (Regent et al, 1985).

EXAMPLE 9

Diagnosis and Prognosis

One possible cancer which might have ASGP-2 is the ascites form of ovarian tumors which occur in the terminal stages of the disease. The applicants' work in animals suggests that the presence of ASGP-2 and p185 in a tumor will make it highly malignant and metastatic. Thus, it would be important to identify those patients with tumors which express ASGP-2 for special therapy. This could be done using antibodies against ASGP-2. A rabbit polyclonal antibody against rat ASGP-2 which reacts with ASGP-2 in human tissue sections has been developed and the applicants are also able to prepare either monoclonal or polyclonal antibodies against human ASGP-2.

Antibodies to ASGP-2 were reactive in immunohistochemical protocols with breast carcinoma sections. Seven tumors which were known to be positive for c-erbB2, the receptor for ASGP-2 ligand, were tested. Only one of those tumors tested were positive for ASGP-2.

EXAMPLE 10

Growth Stimulators

Growth factors act as growth stimulators for some normal target tissues. Thus, some growth factors can be used to promote wound healing by stimulating the growth of specific populations of cells in the damaged tissue (Grotendorst, 1991). Recent studies have shown that factors which stimulate p185 will promote growth of certain types of neural cells, such as Schwann cells (Marchionni et al, 1993). These cells are believed critical for regrowth of certain damaged neural tissues, such as those found in spinal cord injuries. Since ASGP-2 can stimulate p185, it is expected to function in the repair of spinal cord injuries. These ideas will be tested in cell culture and rat model systems using ASGP-2 and its analogs. The ligands will be applied to the cultures in solution or topically to injured tissues in solution.

Documents cited hereinabove are incorporated, in their entirety, by reference.

The present invention has been described in some detail for purposes of clarity and understanding. However, one skilled in the art will appreciate from a reading of this disclosure that various changes in form and detail can be made without departing from the true scope of the invention.

What is claimed is:

1. An isolated DNA segment encoding a transmembrane glycoprotein ASGP-2 component of a cell surface sialomucin complex, consisting of the nucleotide sequence SEQ ID NO:1.

2. An isolated DNA segment encoding a transmembrane glycoprotein ASGP-component of a cell surface sialomucin complex, consisting of the nucleotide sequence SEQ ID NO:97.

3. A recombinant DNA molecule comprising an isolated DNA segment encoding a transmembrane glycoprotein ASGP-2 component of a cell surface sialomucin complex, said DNA segment consisting of the nucleotide sequence SEQ ID NO:1, and a vector.

4. The recombinant DNA molecule according to claim 3, wherein said molecule further comprises a promoter operably linked to said DNA segment.

5. A host cell comprising said recombinant DNA molecule according to claim 3.

6. A method of producing a transmembrane protein ASGP-2 component of a cell surface sialomucin complex comprising culturing the host cell according to claim 5 under conditions such that said DNA segment is expressed and said protein is thereby produced and recovering said protein.

* * * * *

SEQUENCE LISTING ( 1 ) GENERAL INFORMATION:

( i i i ) NUMBER OF SEQUENCES: 125

( 2 ) INFORMATION FOR SEQ ID NO:1:

( i ) SEQUENCE CHARACTERISTICS:
        ( A ) LENGTH: 2603 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:1:

```
GCGCCAGTAG TGTGCTGGTA CAGCCCCGGC CGCTTGACAT TTGGTGATCC CCACATCACC        60
ACTTTGGATA ACGCCAAATA CACCTTCAAC GGGCTAGGAT ACTTCCTGCT GGTTCAGGCC       120
CAGGACAGAA ATTCTTCCTT CCTGCTGGAG GGCCGCACTG CCCAGACTGA TTCTGCCAAT       180
GCCACGAACT TCATTGCCTT TGCGGCCCAA TACAACACCA GCAGCCTGAA GTCTCCATC        240
ACAGTTCAGT GGTTTCTTGA GCCCAATGAC ACAATCCGAG TTGTACACAA TAACCAAACG       300
GTGGCCTTTA ACACCAGCGA CACTGAAGAC TTGCCCGTAT TCAATGCCAC TGGTGTCCTA       360
CTGATCCAAA ATGGCTCCCA AGTCTCAGCC AACTTTGATG GGACAGTGAC CATCTCTGTG       420
ATTGCTCTCT CCAACATCCT TCACGCCTCC TCCAGCCTGT CAGAGGAGTA CCGCAACCAC       480
ACAAAGGGCC TTCTGGGAGT CTGGAATGAC AATCCAGAAG ATGACTTCAG AATGCCCAAT       540
GGCTCCACCA TCCCCTCCAA CACGTCCGAG GAGACTCTTT TCCACTATGG AATGACATCG       600
GAAACTAACG GGATAGGCCT CCTTGGGGTG AGGACAGACC CTCTGCCTTC TGAGTTTACT       660
CCCATCTTCT TGTCCCAACT GTGGAACAAG AGCGGCGCCG GTGAAGACTT GATCTCTGGG       720
TGCAACGAGG ACGCACAGTG CAAGTTTGAC ATCCTGGCCA CAGGAAACAG AGACATCGGA       780
CAAAGCACCA ACTCAATCCT TAGAACATTC CGGCACGTGA ATGGCACGCT CAACCAGTAC       840
CCACCCCCTA TCCACTACAG CAGCAAGATT CAAGCCTACA AGGGGCGAGA ACAGTGGCCA       900
TTGAGATCAC CAGCAACTCT AAGGATGTCG TATTCAGCCT CTCCAACAAG TGCAGTGGCC       960
TTTGAGCTCT TTGAAAACGG GAGTTTGCAC GTGGACACCA ACATCCCCAG AAGAACGTAC      1020
CTGGAGATTC TAGCAAGGGA TGTCAAGACT AACTTGTCAT CGGTACTCCA GCCTGAGACG      1080
GTGGCTTGCT TCTGTAGTAA GGAGGAACAG TGTTTGTACA ACGAGACCAG CAAAGAGGGC      1140
AACTCTTCCA CTGAGGTGAC CAGCTGCAAG TGCGATGGGA ACTCCTTCGG CCGCTTGTGT      1200
GAACACTCTA AGGACCTCTG CACTGAGCCA TGCTTCCCTA ATGTGGACTG CATTCCTGGG      1260
AAGGGCTGTC AGGCCTGCCC TCCAAACATG ACTGGAGATG GCGTCATTG TGTAGCTGTG      1320
GAGATCTCTG AATTCTGCCA GAACCATTCC TGTCCTGTGA ATTACTGTTA TAACCATGGC      1380
CATTGCGACA TCTCTGGGCC TCCAGACTGC CAGCCCACTT GCACCTGCGC CCCTGCCTTC      1440
ACTGGTAACC GCTGCTTCCT GGCCGGGAAC AATTTCACTC CCATCATCTA TAAAGAGCTT      1500
CCCTTGAGGA CCATCACGCT CTCTCTCAGG GAGGACGAAA ACGCCTCTAA CGCTGACGTC      1560
AATGCCTCGG TGGCAAACGT ACTAGAGAAC TTGGACATGC GGGCTTTTCT CTCCAACAGC      1620
TTAGTGGAGC TGATACGAAC CTCTCCCGGA GCACCAGTCC TTGGCAAGCC CATTCATCAC      1680
```

-continued

| | | | | | |
|---|---|---|---|---|---|
| TGGAAGGTCG | TCTCCCACTT | CAAGTACCGT | CCCAGGGGAC | CCCTCATCCA | CTATCTGAAC | 1740 |
| AACCAACTGA | TAAGCGCCGT | GATGGAGGCC | TTCCTCCTCC | AGGCTCGGCA | GGAGAGGCGG | 1800 |
| AAGAGGAGTG | GAGAAGCCAG | GAAGAACGTC | CGCTTCTTCC | CCATCTCGAG | GGCAGACGTC | 1860 |
| CAGGACGGGA | TGGCCCTGAA | CCTAAGTATG | CTGGACGAGT | ACTTCACGTG | CGATGGCTAC | 1920 |
| AAAGGCTACC | ACTTGGTCTA | CAGCCCCCAG | GATGGCGTCA | CCTGTGTGTC | CCCATGTAGT | 1980 |
| GAGGGCTACT | GTCACAATGG | AGGCCAATGC | AAGCACCTGC | CAGATGGGCC | CCAGTGCACG | 2040 |
| TGCGCAACCT | TCAGCATCTA | CACATCCTGG | GGCGAACGCT | GTGAGCATCT | AAGCGTGAAA | 2100 |
| CTTGGGGCAT | TCTTCGGGAT | CCTCTTTGGA | GCCCTGGGTG | CCCTCTTGCT | ACTGGCCATC | 2160 |
| TTAGCATGTG | TGGTCTTTCA | CTTCTGCGGC | TGCTCCATGA | ACAAGTTCTC | CTACCCTCTG | 2220 |
| GACTCAGAAC | TGTGAGGCCT | CGTCCCAGAT | GGGCAGCTGC | ACCTAGAATA | CCTCAGGACC | 2280 |
| CGCCCACCGG | TCTGCCCCTG | CTCTAGGGAG | ACTGGAAAGG | GCCGACTCGA | TGAAGATGAT | 2340 |
| TTGAGATTCT | TCAAGCATGA | ATAAAGGGAG | TGAAACCAGA | CTCTACCATT | TTAGTAGGCC | 2400 |
| ATGGGTATAG | GTTTTCCGGA | GATGAGGAAA | TGTAGAGATG | GATGGATTCC | TATACAGCAC | 2460 |
| ATGGGAAAGG | ATATTGCCTA | TGTACACACA | CACACACACA | CACACCAGAG | TTAATGGATG | 2520 |
| ACTGGCTTTA | TATTCACCAA | AATGTTTTTA | CTTATAAAAC | CAGCATACTT | CTCATTAAAA | 2580 |
| TCTATTTAAA | TATAAAAAAA | AAA | | | | 2603 |

( 2 ) INFORMATION FOR SEQ ID NO:2:

( i ) SEQUENCE CHARACTERISTICS:
        ( A ) LENGTH: 744 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala  Pro  Val  Val  Cys  Trp  Tyr  Ser  Pro  Gly  Arg  Leu  Thr  Phe  Gly  Asp
 1              5                        10                       15

Pro  His  Ile  Thr  Thr  Leu  Asp  Asn  Ala  Lys  Tyr  Thr  Phe  Asn  Gly  Leu
              20                        25                       30

Gly  Tyr  Phe  Leu  Leu  Val  Gln  Ala  Gln  Asp  Arg  Asn  Ser  Ser  Phe  Leu
         35                        40                       45

Leu  Glu  Gly  Arg  Thr  Ala  Gln  Thr  Asp  Ser  Ala  Asn  Ala  Thr  Asn  Phe
     50                        55                       60

Ile  Ala  Phe  Ala  Ala  Gln  Tyr  Asn  Thr  Ser  Ser  Leu  Lys  Ser  Pro  Ile
 65                       70                       75                       80

Thr  Val  Gln  Trp  Phe  Leu  Glu  Pro  Asn  Asp  Thr  Ile  Arg  Val  Val  His
                   85                        90                       95

Asn  Asn  Gln  Thr  Val  Ala  Phe  Asn  Thr  Ser  Asp  Thr  Glu  Asp  Leu  Pro
              100                       105                      110

Val  Phe  Asn  Ala  Thr  Gly  Val  Leu  Leu  Ile  Gln  Asn  Gly  Ser  Gln  Val
         115                       120                      125

Ser  Ala  Asn  Phe  Asp  Gly  Thr  Val  Thr  Ile  Ser  Val  Ile  Ala  Leu  Ser
     130                       135                      140

Asn  Ile  Leu  His  Ala  Ser  Ser  Leu  Ser  Glu  Glu  Tyr  Arg  Asn  His
145                       150                       155                      160

Thr  Lys  Gly  Leu  Leu  Gly  Val  Trp  Asn  Asp  Asn  Pro  Glu  Asp  Asp  Phe
                   165                       170                      175

Arg  Met  Pro  Asn  Gly  Ser  Thr  Ile  Pro  Ser  Asn  Thr  Ser  Glu  Glu  Thr
              180                       185                      190
```

| Leu | Phe | His | Tyr     | Gly | Met | Thr | Ser     | Glu | Thr | Asn | Gly     | Ile | Gly | Leu | Leu |
|     |     |     | 195     |     |     |     | 200     |     |     |     | 205     |     |     |     |     |
| Gly | Val | Arg | Thr     | Asp | Pro | Leu | Pro     | Ser | Glu | Phe | Thr     | Pro | Ile | Phe | Leu |
|     | 210 |     |         |     |     | 215 |         |     |     |     | 220     |     |     |     |     |
| Ser | Gln | Leu | Trp     | Asn | Lys | Ser | Gly     | Ala | Gly | Glu | Asp     | Leu | Ile | Ser | Gly |
| 225 |     |     |         |     | 230 |     |         |     |     | 235 |         |     |     |     | 240 |
| Cys | Asn | Glu | Asp     | Ala | Gln | Cys | Lys     | Phe | Asp | Ile | Leu     | Ala | Thr | Gly | Asn |
|     |     |     |         | 245 |     |     |         |     | 250 |     |         |     |     | 255 |     |
| Arg | Asp | Ile | Gly     | Gln | Ser | Thr | Asn     | Ser | Ile | Leu | Arg     | Thr | Phe | Arg | His |
|     |     |     | 260     |     |     |     |         | 265 |     |     |         |     | 270 |     |     |
| Val | Asn | Gly | Thr     | Leu | Asn | Gln | Tyr     | Pro | Pro | Pro | Ile     | His | Tyr | Ser | Ser |
|     |     | 275 |         |     |     |     | 280     |     |     |     |         | 285 |     |     |     |
| Lys | Ile | Gln | Ala     | Tyr | Lys | Gly | Arg     | Glu | Gln | Trp | Pro     | Leu | Arg | Ser | Pro |
|     | 290 |     |         |     |     |     | 295     |     |     |     | 300     |     |     |     |     |
| Ala | Thr | Leu | Arg     | Met | Ser | Tyr | Ser     | Ala | Ser | Pro | Thr     | Ser | Ala | Val | Ala |
| 305 |     |     |         |     | 310 |     |         |     |     | 315 |         |     |     |     | 320 |
| Phe | Glu | Leu | Phe     | Glu | Asn | Gly | Ser     | Leu | His | Val | Asp     | Thr | Asn | Ile | Pro |
|     |     |     | 325     |     |     |     |         |     | 330 |     |         |     |     | 335 |     |
| Arg | Arg | Thr | Tyr     | Leu | Glu | Ile | Leu     | Ala | Arg | Asp | Val     | Lys | Thr | Asn | Leu |
|     |     |     | 340     |     |     |     |         | 345 |     |     |         |     | 350 |     |     |
| Ser | Ser | Val | Leu     | Gln | Pro | Glu | Thr     | Val | Ala | Cys | Phe     | Cys | Ser | Lys | Glu |
|     |     | 355 |         |     |     |     | 360     |     |     |     |         | 365 |     |     |     |
| Glu | Gln | Cys | Leu     | Tyr | Asn | Glu | Thr     | Ser | Lys | Glu | Gly     | Asn | Ser | Ser | Thr |
|     | 370 |     |         |     |     |     | 375     |     |     |     | 380     |     |     |     |     |
| Glu | Val | Thr | Ser     | Cys | Lys | Cys | Asp     | Gly | Asn | Ser | Phe     | Gly | Arg | Leu | Cys |
| 385 |     |     |         |     | 390 |     |         |     |     | 395 |         |     |     |     | 400 |
| Glu | His | Ser | Lys     | Asp | Leu | Cys | Thr     | Glu | Pro | Cys | Phe     | Pro | Asn | Val | Asp |
|     |     |     |         | 405 |     |     |         |     | 410 |     |         |     |     | 415 |     |
| Cys | Ile | Pro | Gly     | Lys | Gly | Cys | Gln     | Ala | Cys | Pro | Pro     | Asn | Met | Thr | Gly |
|     |     |     | 420     |     |     |     |         | 425 |     |     |         |     | 430 |     |     |
| Asp | Gly | Arg | His     | Cys | Val | Ala | Val     | Glu | Ile | Ser | Glu     | Phe | Cys | Gln | Asn |
|     |     |     | 435     |     |     |     |         | 440 |     |     |         |     | 445 |     |     |
| His | Ser | Cys | Pro     | Val | Asn | Tyr | Cys     | Tyr | Asn | His | Gly     | His | Cys | Asp | Ile |
|     | 450 |     |         |     |     |     | 455     |     |     |     | 460     |     |     |     |     |
| Ser | Gly | Pro | Pro     | Asp | Cys | Gln | Pro     | Thr | Cys | Thr | Cys     | Ala | Pro | Ala | Phe |
| 465 |     |     |         |     | 470 |     |         |     |     | 475 |         |     |     |     | 480 |
| Thr | Gly | Asn | Arg     | Cys | Phe | Leu | Ala     | Gly | Asn | Asn | Phe     | Thr | Pro | Ile | Ile |
|     |     |     |         | 485 |     |     |         |     | 490 |     |         |     |     | 495 |     |
| Tyr | Lys | Glu | Leu     | Pro | Leu | Arg | Thr     | Ile | Thr | Leu | Ser     | Leu | Arg | Glu | Asp |
|     |     |     | 500     |     |     |     |         | 505 |     |     |         |     | 510 |     |     |
| Glu | Asn | Ala | Ser     | Asn | Ala | Asp | Val     | Asn | Ala | Ser | Val     | Ala | Asn | Val | Leu |
|     |     |     | 515     |     |     |     | 520     |     |     |     | 525     |     |     |     |     |
| Glu | Asn | Leu | Asp     | Met | Arg | Ala | Phe     | Leu | Ser | Asn | Ser     | Leu | Val | Glu | Leu |
|     | 530 |     |         |     |     | 535 |         |     |     |     | 540     |     |     |     |     |
| Ile | Arg | Thr | Ser     | Pro | Gly | Ala | Pro     | Val | Leu | Gly | Lys     | Pro | Ile | His | His |
| 545 |     |     |         |     | 550 |     |         |     |     | 555 |         |     |     |     | 560 |
| Trp | Lys | Val | Val     | Ser | His | Phe | Lys     | Tyr | Arg | Pro | Arg     | Gly | Pro | Leu | Ile |
|     |     |     |         | 565 |     |     |         |     | 570 |     |         |     |     | 575 |     |
| His | Tyr | Leu | Asn     | Asn | Gln | Leu | Ile     | Ser | Ala | Val | Met     | Glu | Ala | Phe | Leu |
|     |     |     | 580     |     |     |     |         | 585 |     |     |         |     | 590 |     |     |
| Leu | Gln | Ala | Arg     | Gln | Glu | Arg | Arg     | Lys | Arg | Ser | Gly     | Glu | Ala | Arg | Lys |
|     |     | 595 |         |     |     |     | 600     |     |     |     |         | 605 |     |     |     |
| Asn | Val | Arg | Phe     | Phe | Pro | Ile | Ser     | Arg | Ala | Asp | Val     | Gln | Asp | Gly | Met |

```
                    610                           615                            620

Ala   Leu   Asn   Leu   Ser   Met   Leu   Asp   Glu   Tyr   Phe   Thr   Cys   Asp   Gly   Tyr
625                           630                           635                           640

Lys   Gly   Tyr   His   Leu   Val   Tyr   Ser   Pro   Gln   Asp   Gly   Val   Thr   Cys   Val
                        645                           650                           655

Ser   Pro   Cys   Ser   Glu   Gly   Tyr   Cys   His   Asn   Gly   Gly   Gln   Cys   Lys   His
                  660                           665                           670

Leu   Pro   Asp   Gly   Pro   Gln   Cys   Thr   Cys   Ala   Thr   Phe   Ser   Ile   Tyr   Thr
            675                           680                           685

Ser   Trp   Gly   Glu   Arg   Cys   Glu   His   Leu   Ser   Val   Lys   Leu   Gly   Ala   Phe
      690                           695                           700

Phe   Gly   Ile   Leu   Phe   Gly   Ala   Leu   Gly   Ala   Leu   Leu   Leu   Leu   Ala   Ile
705                           710                           715                           720

Leu   Ala   Cys   Val   Val   Phe   His   Phe   Cys   Gly   Cys   Ser   Met   Asn   Lys   Phe
                        725                           730                           735

Ser   Tyr   Pro   Leu   Asp   Ser   Glu   Leu
                  740
```

( 2 ) INFORMATION FOR SEQ ID NO:3:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

```
Pro   Val   Asn   Tyr   Val   Tyr   Asn   His   Gly   His   Cys   Phe   Asp   Ile   Ser   Gly
1                       5                             10                            15

Pro   Pro   Asp   Cys   Gln   Pro   Thr   Cys   Thr   Cys   Ala   Pro   Ala   Gly
                  20                        25                        30
```

( 2 ) INFORMATION FOR SEQ ID NO:4:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

```
Gly   Asn   Arg   Cys   Phe   Leu   Ala   Gly   Asn
1                       5
```

( 2 ) INFORMATION FOR SEQ ID NO:5:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

```
Ser   Glu   Gly   Tyr   Cys   His   Asn   Gly   Gly   Gln   Cys
1                       5                             10
```

( 2 ) INFORMATION FOR SEQ ID NO:6:

( i ) SEQUENCE CHARACTERISTICS:
                ( A ) LENGTH: 30 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:6:

Lys His Leu Pro Asp Gly Pro Gln Cys Thr Cys Ala Thr Phe Ser Ile
    1               5                   10                  15

Tyr Thr Ser Trp Gly Glu Arg Cys Glu His Leu Ser Val Lys
                20                  25                  30

( 2 ) INFORMATION FOR SEQ ID NO:7:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:7:

Gly Pro Gly Gly Cys Gly Ser His Ala Arg Cys
    1               5                   10

( 2 ) INFORMATION FOR SEQ ID NO:8:

( i ) SEQUENCE CHARACTERISTICS:
                ( A ) LENGTH: 17 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:8:

Val Ser Asp Gly Glu Thr Ala Glu Cys Gln Cys Lys Leu Gly Arg Ala
    1               5                   10                  15

Arg ( 2 ) INFORMATION FOR SEQ ID NO:9:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:9:

Gly Asn Leu Cys Ser Asp Ile Asp Glu
    1               5

( 2 ) INFORMATION FOR SEQ ID NO:10:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:10:

Thr Glu Ser Ser Cys Leu Asn Gly Gly Ser Cys ( 2 ) INFORMATION FOR SEQ ID NO:11:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Ile  Asp  Gly  Ile  Asn  Gly  Tyr  Asn  Cys  Ser  Cys  Leu  Ala  Gly  Tyr
1                   5                        10                       15
```

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Gly  Ala  Asn  Cys  Gln  Tyr
1                   5
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Leu  Glu  Asn  Pro  Cys  Ser  Asn  Gly  Gly  Val  Cys
1                   5                        10
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
His  Gln  His  Arg  Glu  Ser  Phe  Ser  Cys  Glu  Cys  Pro  Pro  Gly  Phe
1                   5                        10                       15
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Gly  Asn  Gly  Cys  Glu  Gln
```

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Glu  Ser  Asn  Pro  Cys  Leu  Asn  Gly  Gly  Ser  Cys
 1              5                             10
```

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Lys  Asp  Asp  Ile  Asn  Ser  Tyr  Glu  Cys  Trp  Cys  Pro  Phe  Gly  Phe
 1              5                             10                            15
```

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Gly  Lys  Asn  Cys  Glu  Leu  Asp  Val  Thr
 1              5
```

(2) INFORMATION FOR SEQ ID NO:19:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Glu  Thr  Ser  Pro  Cys  Gln  Asn  Gln  Gly  Lys  Cys
 1              5                             10
```

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Lys  Asp  Gly  Leu  Gly  Glu  Tyr  Thr  Cys  Thr  Cys  Leu  Leu  Gly  Phe
```

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Gly Lys Asn Cys Glu Leu Phe Thr Arg Lys
 1               5                  10
```

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Arg Thr Asn Pro Cys Leu His Gly Gly Arg Cys
 1               5                  10
```

(2) INFORMATION FOR SEQ ID NO:23:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Leu Glu Val Glu Gly His Arg Leu Cys His Cys Pro Val Gly Tyr
 1               5                  10                  15
```

(2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Gly Pro Phe Cys Asp Val
 1               5
```

(2) INFORMATION FOR SEQ ID NO:25:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Leu Asp Asn Asn Gly Gly Cys Ser His Val Cys
```

1                    5                              10

(2) INFORMATION FOR SEQ ID NO:26:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Asn  Asp  Leu  Lys  Ile  Gly  Tyr  Glu  Cys  Leu  Cys  Pro  Asp  Gly  Phe  Gln
1                   5                             10                            15

Leu  Val  Ala (2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Gln  Arg  Arg  Cys  Glu  Asp  Ile  Asp  Glu
1                   5

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Gln  Pro  Trp  Ser  Cys  Ser  Gly  His  Gly  Glu  Cys
1                   5                             10

(2) INFORMATION FOR SEQ ID NO:29:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Val  Gly  Ile  Ile  Asn  Asn  His  Thr  Cys  Asn  Cys  Asp  Val  Gly  Tyr
1                   5                             10                            15

(2) INFORMATION FOR SEQ ID NO:30:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
        Gly  Pro  Gln  Cys  Gln
        1                   5
```

( 2 ) INFORMATION FOR SEQ ID NO:31:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
        Lys  Met  Asn  Pro  Cys  Leu  Asn  Gly  Gly  Cys
        1                   5                        10
```

( 2 ) INFORMATION FOR SEQ ID NO:32:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
        Tyr  Pro  Thr  Glu  Thr  Ser  Tyr  Val  Cys  Thr  Cys  Val  Pro  Gly  Tyr
        1                   5                        10                       15
```

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
        Gly  Asp  Cys  Glu  Leu  Asp  Phe  Asp  Glu
        1                   5
```

( 2 ) INFORMATION FOR SEQ ID NO:34:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

```
        His  Ser  Asn  Pro  Cys  Arg  Asn  Gly  Ala  Thr  Cys
        1                   5                        10
```

( 2 ) INFORMATION FOR SEQ ID NO:35:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

```
        Val  Asp  Gly  Phe  Asn  Thr  Phe  Arg  Cys  Leu  Cys  Leu  Pro  Ser  Tyr
        1                   5                        10                       15
```

( 2 ) INFORMATION FOR SEQ ID NO:36:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

```
        Gly  Ala  Leu  Cys  Glu  Gln  Asp  Thr  Glu  Thr
        1                   5                        10
```

( 2 ) INFORMATION FOR SEQ ID NO:37:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

```
        Cys  Pro  Asp  Gly  Pro  Asp  Ser  Gly  Arg  Gln  Phe  Ala  Arg  Ser  Cys  Tyr
        1                   5                        10                       15

Gln  Asp  Pro  Val  Thr  Leu  Gln
                            20
```

( 2 ) INFORMATION FOR SEQ ID NO:38:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
        Leu  Ala  Cys  Val  Cys  Asp  Pro  Gly  Tyr
        1                   5
```

( 2 ) INFORMATION FOR SEQ ID NO:39:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
        Gly  Ser  Arg  Cys  Asp  Asp  Cys  Ala  Ser  Gly
        1                   5                        10
```

( 2 ) INFORMATION FOR SEQ ID NO:40:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:40:

Asn Pro Tyr Gly Thr Met Lys Gln Gln Ser Ser Cys
1               5                   10

(2) INFORMATION FOR SEQ ID NO:41:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:41:

Asn Pro Val Thr Gly Gln
1               5

(2) INFORMATION FOR SEQ ID NO:42:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:42:

Cys Glu Cys Leu Pro His Val
1               5

(2) INFORMATION FOR SEQ ID NO:43:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:43:

Gly Gln Asp Cys Gly Ala Cys Asp Pro Gly
1               5                   10

(2) INFORMATION FOR SEQ ID NO:44:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:44:

Asp Ser Ser Leu Cys Leu Asn Gly Gly Thr Cys
1               5                   10

(2) INFORMATION FOR SEQ ID NO:45:

(i) SEQUENCE CHARACTERISTICS:
        (A) LENGTH: 15 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:45:

```
Leu Thr Gly Gln Asn Asp Ile Tyr Cys Leu Cys Pro Glu Gly Phe
  1               5                  10                  15
```

( 2 ) INFORMATION FOR SEQ ID NO:46:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

```
Gly Leu Val Cys Asn
  1           5
```

( 2 ) INFORMATION FOR SEQ ID NO:47:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

```
Ser Pro Asn Pro Cys Tyr Asn Asp Ala Lys Cys
  1           5                   10
```

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

```
Tyr Ile Cys Gln Cys Pro Val Gly Tyr
  1           5
```

( 2 ) INFORMATION FOR SEQ ID NO:49:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

```
Gly Ile His Cys Glu
  1           5
```

( 2 ) INFORMATION FOR SEQ ID NO:50:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

```
Glu Phe Cys Gln Asn His Ser Cys Pro
1               5
```

( 2 ) INFORMATION FOR SEQ ID NO:51:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
Val Asn Tyr Cys Tyr Asn His Gly His Cys Asp Ile Ser Gly Pro
1               5                   10                  15
```

( 2 ) INFORMATION FOR SEQ ID NO:52:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

```
Pro Asp Cys Gln Pro Thr Cys Thr Cys Ala Pro Ala Phe Thr
1               5                   10
```

( 2 ) INFORMATION FOR SEQ ID NO:53:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:53:

```
Gly Asn Arg Cys Phe Leu Ala Gly Asn Asn Phe Thr Pro Ile
1               5                   10
```

( 2 ) INFORMATION FOR SEQ ID NO:54:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:54:

```
Gly Val Thr Cys Val Ser Pro Cys Ser
1               5
```

( 2 ) INFORMATION FOR SEQ ID NO:55:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:55:

```
Glu Gly Tyr Cys His Asn Gly Gly Gln Cys Lys His Leu
 1               5                   10
```

( 2 ) INFORMATION FOR SEQ ID NO:56:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:56:

```
Pro Gln Cys Thr Cys Ala Thr Phe Ser Ile Tyr Thr Ser Trp Gly Glu
 1               5                   10                  15

Arg Cys Glu His Leu Ser Val Lys
                20
```

( 2 ) INFORMATION FOR SEQ ID NO:57:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:57:

```
Asn Ser Asp Ser Glu Cys Pro Leu Ser His Asp Gly Tyr Cys Leu His
 1               5                   10                  15

Asp Gly Val Cys Met Tyr Ile Glu Ala
                20                  25
```

( 2 ) INFORMATION FOR SEQ ID NO:58:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

```
Leu Lys Asp Tyr Ala Cys Asn Cys Val Val Gly Tyr Ile
 1               5                   10
```

( 2 ) INFORMATION FOR SEQ ID NO:59:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

```
Gly Glu Arg Cys Gln Tyr Arg Asp Leu Lys Trp Trp Glu Leu Arg
 1               5                   10                  15
```

( 2 ) INFORMATION FOR SEQ ID NO:60:

( i ) SEQUENCE CHARACTERISTICS:
   ( A ) LENGTH: 25 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:60:

Asn Ser Tyr Pro Gly Cys Pro Ser Ser Tyr Asp Gly Tyr Cys Leu Asn
1               5                   10                  15

Gly Gly Val Cys Met His Ile Glu Ser
            20              25

( 2 ) INFORMATION FOR SEQ ID NO:61:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:61:

Leu Asp Ser Tyr Thr Cys Asn Cys Val Ile Gly Tyr Ser
1               5                   10

( 2 ) INFORMATION FOR SEQ ID NO:62:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:62:

Gly Asp Arg Cys Gln Thr Arg Asp Leu Arg Trp Trp Glu Leu Arg
1               5                   10                  15

( 2 ) INFORMATION FOR SEQ ID NO:63:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:63:

Asn Ser Asn Thr Gly Cys Pro Pro Ser Tyr Asp Gly Tyr Cys Leu Asn
1               5                   10                  15

Gly Gly Val Cys Met Tyr Val Glu Ser
            20              25

( 2 ) INFORMATION FOR SEQ ID NO:64:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:64:

```
Val  Asp  Arg  Tyr  Val  Cys  Asn  Cys  Val  Ile  Gly  Tyr  Tyr  Ile
1              5                        10
```

( 2 ) INFORMATION FOR SEQ ID NO:65:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:65:

```
Gly  Glu  Arg  Cys  His  Arg  Asp  Leu  Arg
1                   5
```

( 2 ) INFORMATION FOR SEQ ID NO:66:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:66:

```
Gln  Asp  Ala  Pro  Gly  Cys  Pro  Pro  Ser  His  Asp  Gly  Tyr  Cys  Leu  His
1                   5                        10                       15

Gly  Gly  Val  Cys  Met  His  Ile  Glu  Ser
                20                       25
```

( 2 ) INFORMATION FOR SEQ ID NO:67:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:67:

```
Leu  Asn  Thr  Tyr  Ala  Cys  Asn  Cys  Val  Ile  Gly  Tyr  Val
1                   5                        10
```

( 2 ) INFORMATION FOR SEQ ID NO:68:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:68:

```
Gly  Glu  Arg  Cys  Glu  His  Gln  Asp  Leu  Asp  Trp  Glu
1                   5                        10
```

( 2 ) INFORMATION FOR SEQ ID NO:69:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:69:

Val Val Ser His Phe Asn Asp Cys Pro Asp Ser His Thr Gln Phe Cys
1               5                   10                  15

Phe ( 2 ) INFORMATION FOR SEQ ID NO:70:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:70:

His Gln Thr Cys Arg Phe Leu Val Gln
1               5

( 2 ) INFORMATION FOR SEQ ID NO:71:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:71:

Glu Asp Lys Pro Ala Cys Val Cys His Ser Gly Tyr Val
1               5                   10

( 2 ) INFORMATION FOR SEQ ID NO:72:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:72:

Gly Ala Arg Cys Glu His Ala Asp Leu Leu Ala
1               5                   10

( 2 ) INFORMATION FOR SEQ ID NO:73:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:73:

Val Val Ser His Phe Asn Lys Cys Pro Asp Ser His Thr Gln Tyr Cys
1               5                   10                  15

Phe ( 2 ) INFORMATION FOR SEQ ID NO:74:

( i ) SEQUENCE CHARACTERISTICS:
      ( A ) LENGTH: 9 amino acids
      ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:74:

His Gly Thr Cys Arg Phe Leu Val Gln
1               5

( 2 ) INFORMATION FOR SEQ ID NO:75:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:75:

Glu Glu Lys Pro Ala Cys Val Cys His Ser Gly Tyr Val
1               5                   10

( 2 ) INFORMATION FOR SEQ ID NO:76:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:76:

Gly Val Arg Cys Glu His Ala Asp Leu Leu Ala
1               5                   10

( 2 ) INFORMATION FOR SEQ ID NO:77:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:77:

Asp Ile Pro Ala Ile Arg Leu Cys Gly Pro Glu Gly Asp Gly Tyr Cys
1               5                   10                  15

Leu ( 2 ) INFORMATION FOR SEQ ID NO:78:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:78:

His Gly Asp Cys Ile His Ala Arg Asp
1               5

( 2 ) INFORMATION FOR SEQ ID NO:79:

( i ) SEQUENCE CHARACTERISTICS:

(A) LENGTH: 13 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:79:

Ile Asp Gly Met Tyr Cys Arg Cys Ser His Gly Tyr Thr
1               5                       10

(2) INFORMATION FOR SEQ ID NO:80:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:80:

Gly Ile Arg Cys Gln His Val Val Leu Val Asp Tyr Gln Arg Ser
1               5                       10                      15

(2) INFORMATION FOR SEQ ID NO:81:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:81:

Ile Val Lys His Val Lys Val Cys Asn His Asp Tyr Glu Asn Tyr Cys
1               5                       10                      15

Leu Asn Asn Gly Thr Cys Phe Thr Ile Ala Leu Asp Asn Val Ser Ile
                20                      25                      30

Thr Pro Phe Cys Val Cys Arg Ile Asn Tyr Glu
            35                      40

(2) INFORMATION FOR SEQ ID NO:82:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:82:

Gly Ser Arg Cys Gln Phe Ile Asn Leu Val Thr Tyr
1               5                       10

(2) INFORMATION FOR SEQ ID NO:83:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:83:

Ile Ile Lys Arg Ile Lys Leu Cys Asn Asp Asp Tyr Lys Asn Tyr Cys

```
                1               5                      10                          15
           Leu Asn Asn Gly Thr Cys Phe Thr Val Ala Leu Asn Asn Val Ser Leu
                           20                  25                  30

Asn Pro Phe Cys Ala Cys His Ile Asn Tyr Val
                       35                  40
```

( 2 ) INFORMATION FOR SEQ ID NO:84:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:84:

```
           Gly Ser Arg Cys Gln Phe Ile Asn Leu Ile Thr Ile Lys
           1               5                       10
```

( 2 ) INFORMATION FOR SEQ ID NO:85:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:85:

```
           Lys Lys Arg Asp Pro Cys Leu Arg Lys Tyr Lys Asp Phe Cys Ile
           1               5                       10                          15
```

( 2 ) INFORMATION FOR SEQ ID NO:86:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:86:

```
           His Gly Glu Cys Lys Tyr Val Lys Glu
           1               5
```

( 2 ) INFORMATION FOR SEQ ID NO:87:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:87:

```
           Leu Arg Ala Pro Ser Cys Ile Cys His Pro Gly Tyr His
           1               5                       10
```

( 2 ) INFORMATION FOR SEQ ID NO:88:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:88:

Gly Glu Arg Cys His Gly Leu Ser Leu
1               5

( 2 ) INFORMATION FOR SEQ ID NO:89:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:89:

Asn Arg Lys Lys Lys Asn Pro Cys Asn Ala Glu Phe Gln Asn Phe Cys
1               5                   10                  15

Ile ( 2 ) INFORMATION FOR SEQ ID NO:90:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:90:

His Gly Glu Cys Lys Tyr Ile Glu His
1               5

( 2 ) INFORMATION FOR SEQ ID NO:91:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:91:

Leu Glu Ala Val Thr Cys Lys Cys Gln Gln Glu Tyr Phe
1               5                   10

( 2 ) INFORMATION FOR SEQ ID NO:92:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:92:

Gly Glu Arg Cys Gly Glu Lys Ser Asn Lys Thr His Ser Asn Ile
1               5                   10                  15

( 2 ) INFORMATION FOR SEQ ID NO:93:

( i ) SEQUENCE CHARACTERISTICS:
    ( A ) LENGTH: 14 amino acids
    ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:93:

```
Xaa Xaa Ile Thr Thr Leu Asp Asn Ala Lys Tyr Thr Phe Asn
1               5                   10
```

(2) INFORMATION FOR SEQ ID NO:94:

(i) SEQUENCE CHARACTERISTICS:
    (A) LENGTH: 19 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:94:

```
Met Arg Ala Phe Leu Ser Asn Ser Leu Val Glu Leu Ile Arg Thr Ser
1               5                   10                  15

Pro Gly Ala
```

(2) INFORMATION FOR SEQ ID NO:95:

(i) SEQUENCE CHARACTERISTICS:
    (A) LENGTH: 24 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:95:

```
Cys Xaa Xaa Xaa Xaa Cys Xaa Xaa Xaa Xaa Xaa Cys Xaa Cys Xaa Xaa
1               5                   10                  15

Xaa Xaa Xaa Xaa Xaa Xaa Cys Xaa
                20
```

(2) INFORMATION FOR SEQ ID NO:96:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:96:

```
Cys Xaa Cys Xaa Xaa Gly Xaa Xaa Gly Xaa Xaa Cys
1               5                   10
```

(2) INFORMATION FOR SEQ ID NO:97:

(i) SEQUENCE CHARACTERISTICS:
    (A) LENGTH: 2232 base pairs
    (B) TYPE: nucleic acid
    (C) STRANDEDNESS: single
    (D) TOPOLOGY: linear (ii) MOLECULE TYPE: peptide (ix) FEATURE:
    (A) NAME/KEY: CDS
    (B) LOCATION: 1..2232

(xi) SEQUENCE DESCRIPTION: SEQ ID NO:97:

| | | | | | | | | | | | | | | | | |
|---|---|---|---|---|---|---|---|---|---|---|---|---|---|---|---|---|
| GCG | CCA | GTA | GTG | TGC | TGG | TAC | AGC | CCC | GGC | CGC | TTG | ACA | TTT | GGT | GAT | 48 |
| Ala | Pro | Val | Val | Cys | Trp | Tyr | Ser | Pro | Gly | Arg | Leu | Thr | Phe | Gly | Asp | |
| 1 | | | | 5 | | | | | 10 | | | | | 15 | | |
| CCC | CAC | ATC | ACC | ACT | TTG | GAT | AAC | GCC | AAA | TAC | ACC | TTC | AAC | GGG | CTA | 96 |
| Pro | His | Ile | Thr | Thr | Leu | Asp | Asn | Ala | Lys | Tyr | Thr | Phe | Asn | Gly | Leu | |
| | | | 20 | | | | | 25 | | | | | 30 | | | |
| GGA | TAC | TTC | CTG | CTG | GTT | CAG | GCC | CAG | GAC | AGA | AAT | TCT | TCC | TTC | CTG | 144 |
| Gly | Tyr | Phe | Leu | Leu | Val | Gln | Ala | Gln | Asp | Arg | Asn | Ser | Ser | Phe | Leu | |
| | | 35 | | | | | 40 | | | | | 45 | | | | |
| CTG | GAG | GGC | CGC | ACT | GCC | CAG | ACT | GAT | TCT | GCC | AAT | GCC | ACG | AAC | TTC | 192 |
| Leu | Glu | Gly | Arg | Thr | Ala | Gln | Thr | Asp | Ser | Ala | Asn | Ala | Thr | Asn | Phe | |
| 50 | | | | | 55 | | | | | 60 | | | | | | |
| ATT | GCC | TTT | GCG | GCC | CAA | TAC | AAC | ACC | AGC | AGC | CTG | AAG | TCT | CCC | ATC | 240 |
| Ile | Ala | Phe | Ala | Ala | Gln | Tyr | Asn | Thr | Ser | Ser | Leu | Lys | Ser | Pro | Ile | |
| 65 | | | | | 70 | | | | | 75 | | | | | 80 | |
| ACA | GTT | CAG | TGG | TTT | CTT | GAG | CCC | AAT | GAC | ACA | ATC | CGA | GTT | GTA | CAC | 288 |
| Thr | Val | Gln | Trp | Phe | Leu | Glu | Pro | Asn | Asp | Thr | Ile | Arg | Val | Val | His | |
| | | | | 85 | | | | | 90 | | | | | 95 | | |
| AAT | AAC | CAA | ACG | GTG | GCC | TTT | AAC | ACC | AGC | GAC | ACT | GAA | GAC | TTG | CCC | 336 |
| Asn | Asn | Gln | Thr | Val | Ala | Phe | Asn | Thr | Ser | Asp | Thr | Glu | Asp | Leu | Pro | |
| | | | 100 | | | | | 105 | | | | | 110 | | | |
| GTA | TTC | AAT | GCC | ACT | GGT | GTC | CTA | CTG | ATC | CAA | AAT | GGC | TCC | CAA | GTC | 384 |
| Val | Phe | Asn | Ala | Thr | Gly | Val | Leu | Leu | Ile | Gln | Asn | Gly | Ser | Gln | Val | |
| | | 115 | | | | | 120 | | | | | 125 | | | | |
| TCA | GCC | AAC | TTT | GAT | GGG | ACA | GTG | ACC | ATC | TCT | GTG | ATT | GCT | CTC | TCC | 432 |
| Ser | Ala | Asn | Phe | Asp | Gly | Thr | Val | Thr | Ile | Ser | Val | Ile | Ala | Leu | Ser | |
| | | 130 | | | | | 135 | | | | | 140 | | | | |
| AAC | ATC | CTT | CAC | GCC | TCC | TCC | AGC | CTG | TCA | GAG | GAG | TAC | CGC | AAC | CAC | 480 |
| Asn | Ile | Leu | His | Ala | Ser | Ser | Ser | Leu | Ser | Glu | Glu | Tyr | Arg | Asn | His | |
| 145 | | | | | 150 | | | | | 155 | | | | | 160 | |
| ACA | AAG | GGC | CTT | CTG | GGA | GTC | TGG | AAT | GAC | AAT | CCA | GAA | GAT | GAC | TTC | 528 |
| Thr | Lys | Gly | Leu | Leu | Gly | Val | Trp | Asn | Asp | Asn | Pro | Glu | Asp | Asp | Phe | |
| | | | | 165 | | | | | 170 | | | | | 175 | | |
| AGA | ATG | CCC | AAT | GGC | TCC | ACC | ATC | CCC | TCC | AAC | ACG | TCC | GAG | GAG | ACT | 576 |
| Arg | Met | Pro | Asn | Gly | Ser | Thr | Ile | Pro | Ser | Asn | Thr | Ser | Glu | Glu | Thr | |
| | | | 180 | | | | | 185 | | | | | 190 | | | |
| CTT | TTC | CAC | TAT | GGA | ATG | ACA | TCG | GAA | ACT | AAC | GGG | ATA | GGC | CTC | CTT | 624 |
| Leu | Phe | His | Tyr | Gly | Met | Thr | Ser | Glu | Thr | Asn | Gly | Ile | Gly | Leu | Leu | |
| | | | 195 | | | | | 200 | | | | | 205 | | | |
| GGG | GTG | AGG | ACA | GAC | CCT | CTG | CCT | TCT | GAG | TTT | ACT | CCC | ATC | TTC | TTG | 672 |
| Gly | Val | Arg | Thr | Asp | Pro | Leu | Pro | Ser | Glu | Phe | Thr | Pro | Ile | Phe | Leu | |
| 210 | | | | | 215 | | | | | 220 | | | | | | |
| TCC | CAA | CTG | TGG | AAC | AAG | AGC | GGC | GCC | GGT | GAA | GAC | TTG | ATC | TCT | GGG | 720 |
| Ser | Gln | Leu | Trp | Asn | Lys | Ser | Gly | Ala | Gly | Glu | Asp | Leu | Ile | Ser | Gly | |
| 225 | | | | | 230 | | | | | 235 | | | | | 240 | |
| TGC | AAC | GAG | GAC | GCA | CAG | TGC | AAG | TTT | GAC | ATC | CTG | GCC | ACA | GGA | AAC | 768 |
| Cys | Asn | Glu | Asp | Ala | Gln | Cys | Lys | Phe | Asp | Ile | Leu | Ala | Thr | Gly | Asn | |
| | | | | 245 | | | | | 250 | | | | | 255 | | |
| AGA | GAC | ATC | GGA | CAA | AGC | ACC | AAC | TCA | ATC | CTT | AGA | ACA | TTC | CGG | CAC | 816 |
| Arg | Asp | Ile | Gly | Gln | Ser | Thr | Asn | Ser | Ile | Leu | Arg | Thr | Phe | Arg | His | |
| | | | 260 | | | | | 265 | | | | | 270 | | | |
| GTG | AAT | GGC | ACG | CTC | AAC | CAG | TAC | CCA | CCC | CCT | ATC | CAC | TAC | AGC | AGC | 864 |
| Val | Asn | Gly | Thr | Leu | Asn | Gln | Tyr | Pro | Pro | Pro | Ile | His | Tyr | Ser | Ser | |
| | | | 275 | | | | | 280 | | | | | 285 | | | |
| AAG | ATT | CAA | GCC | TAC | AAG | GGG | CGA | GAA | CAG | TGG | CCA | TTG | AGA | TCA | CCA | 912 |
| Lys | Ile | Gln | Ala | Tyr | Lys | Gly | Arg | Glu | Gln | Trp | Pro | Leu | Arg | Ser | Pro | |
| | 290 | | | | | 295 | | | | | 300 | | | | | |
| GCA | ACT | CTA | AGG | ATG | TCG | TAT | TCA | GCC | TCT | CCA | ACA | AGT | GCA | GTG | GCC | 960 |
| Ala | Thr | Leu | Arg | Met | Ser | Tyr | Ser | Ala | Ser | Pro | Thr | Ser | Ala | Val | Ala | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| TTT | GAG | CTC | TTT | GAA | AAC | GGG | AGT | TTG | CAC | GTG | GAC | ACC | AAC | ATC | CCC | 1008 |
| Phe | Glu | Leu | Phe | Glu 325 | Asn | Gly | Ser | Leu | His 330 | Val | Asp | Thr | Asn | Ile 335 | Pro | |
| AGA | AGA | ACG | TAC | CTG | GAG | ATT | CTA | GCA | AGG | GAT | GTC | AAG | ACT | AAC | TTG | 1056 |
| Arg | Arg | Thr | Tyr 340 | Leu | Glu | Ile | Leu | Ala 345 | Arg | Asp | Val | Lys | Thr 350 | Asn | Leu | |
| TCA | TCG | GTA | CTC | CAG | CCT | GAG | ACG | GTG | GCT | TGC | TTC | TGT | AGT | AAG | GAG | 1104 |
| Ser | Ser | Val 355 | Leu | Gln | Pro | Glu | Thr 360 | Val | Ala | Cys | Phe | Cys 365 | Ser | Lys | Glu | |
| GAA | CAG | TGT | TTG | TAC | AAC | GAG | ACC | AGC | AAA | GAG | GGC | AAC | TCT | TCC | ACT | 1152 |
| Glu | Gln 370 | Cys | Leu | Tyr | Asn | Glu 375 | Thr | Ser | Lys | Glu | Gly 380 | Asn | Ser | Ser | Thr | |
| GAG | GTG | ACC | AGC | TGC | AAG | TGC | GAT | GGG | AAC | TCC | TTC | GGC | CGC | TTG | TGT | 1200 |
| Glu 385 | Val | Thr | Ser | Cys | Lys 390 | Cys | Asp | Gly | Asn | Ser 395 | Phe | Gly | Arg | Leu | Cys 400 | |
| GAA | CAC | TCT | AAG | GAC | CTC | TGC | ACT | GAG | CCA | TGC | TTC | CCT | AAT | GTG | GAC | 1248 |
| Glu | His | Ser | Lys | Asp 405 | Leu | Cys | Thr | Glu | Pro 410 | Cys | Phe | Pro | Asn | Val 415 | Asp | |
| TGC | ATT | CCT | GGG | AAG | GGC | TGT | CAG | GCC | TGC | CCT | CCA | AAC | ATG | ACT | GGA | 1296 |
| Cys | Ile | Pro | Gly 420 | Lys | Gly | Cys | Gln | Ala 425 | Cys | Pro | Pro | Asn | Met 430 | Thr | Gly | |
| GAT | GGG | CGT | CAT | TGT | GTA | GCT | GTG | GAG | ATC | TCT | GAA | TTC | TGC | CAG | AAC | 1344 |
| Asp | Gly | Arg 435 | His | Cys | Val | Ala | Val 440 | Glu | Ile | Ser | Glu | Phe 445 | Cys | Gln | Asn | |
| CAT | TCC | TGT | CCT | GTG | AAT | TAC | TGT | TAT | AAC | CAT | GGC | CAT | TGC | GAC | ATC | 1392 |
| His | Ser 450 | Cys | Pro | Val | Asn | Tyr 455 | Cys | Tyr | Asn | His | Gly 460 | His | Cys | Asp | Ile | |
| TCT | GGG | CCT | CCA | GAC | TGC | CAG | CCC | ACT | TGC | ACC | TGC | GCC | CCT | GCC | TTC | 1440 |
| Ser 465 | Gly | Pro | Pro | Asp | Cys 470 | Gln | Pro | Thr | Cys | Thr 475 | Cys | Ala | Pro | Ala | Phe 480 | |
| ACT | GGT | AAC | CGC | TGC | TTC | CTG | GCC | GGG | AAC | AAT | TTC | ACT | CCC | ATC | ATC | 1488 |
| Thr | Gly | Asn | Arg | Cys 485 | Phe | Leu | Ala | Gly | Asn 490 | Asn | Phe | Thr | Pro | Ile 495 | Ile | |
| TAT | AAA | GAG | CTT | CCC | TTG | AGG | ACC | ATC | ACG | CTC | TCT | CTC | AGG | GAG | GAC | 1536 |
| Tyr | Lys | Glu | Leu 500 | Pro | Leu | Arg | Thr | Ile 505 | Thr | Leu | Ser | Leu | Arg 510 | Glu | Asp | |
| GAA | AAC | GCC | TCT | AAC | GCT | GAC | GTC | AAT | GCC | TCG | GTG | GCA | AAC | GTA | CTA | 1584 |
| Glu | Asn | Ala 515 | Ser | Asn | Ala | Asp | Val 520 | Asn | Ala | Ser | Val | Ala 525 | Asn | Val | Leu | |
| GAG | AAC | TTG | GAC | ATG | CGG | GCT | TTT | CTC | TCC | AAC | AGC | TTA | GTG | GAG | CTG | 1632 |
| Glu | Asn | Leu 530 | Asp | Met | Arg | Ala 535 | Phe | Leu | Ser | Asn | Ser 540 | Leu | Val | Glu | Leu | |
| ATA | CGA | ACC | TCT | CCC | GGA | GCA | CCA | GTC | CTT | GGC | AAG | CCC | ATT | CAT | CAC | 1680 |
| Ile 545 | Arg | Thr | Ser | Pro | Gly 550 | Ala | Pro | Val | Leu | Gly 555 | Lys | Pro | Ile | His | His 560 | |
| TGG | AAG | GTC | GTC | TCC | CAC | TTC | AAG | TAC | CGT | CCC | AGG | GGA | CCC | CTC | ATC | 1728 |
| Trp | Lys | Val | Val | Ser 565 | His | Phe | Lys | Tyr | Arg 570 | Pro | Arg | Gly | Pro | Leu 575 | Ile | |
| CAC | TAT | CTG | AAC | AAC | CAA | CTG | ATA | AGC | GCC | GTG | ATG | GAG | GCC | TTC | CTC | 1776 |
| His | Tyr | Leu | Asn 580 | Asn | Gln | Leu | Ile | Ser 585 | Ala | Val | Met | Glu | Ala 590 | Phe | Leu | |
| CTC | CAG | GCT | CGG | CAG | GAG | AGG | CGG | AAG | AGG | AGT | GGA | GAA | GCC | AGG | AAG | 1824 |
| Leu | Gln | Ala | Arg 595 | Gln | Glu | Arg | Arg | Lys 600 | Arg | Ser | Gly | Glu | Ala 605 | Arg | Lys | |
| AAC | GTC | CGC | TTC | TTC | CCC | ATC | TCG | AGG | GCA | GAC | GTC | CAG | GAC | GGG | ATG | 1872 |
| Asn | Val | Arg 610 | Phe | Phe | Pro | Ile | Ser 615 | Arg | Ala | Asp | Val | Gln 620 | Asp | Gly | Met | |
| GCC | CTG | AAC | CTA | AGT | ATG | CTG | GAC | GAG | TAC | TTC | ACG | TGC | GAT | GGC | TAC | 1920 |
| Ala | Leu | Asn 625 | Leu | Ser | Met | Leu | Asp 630 | Glu | Tyr | Phe | Thr | Cys 635 | Asp | Gly | Tyr 640 | |

| | | | | | | | | | | | | | | | | |
|---|---|---|---|---|---|---|---|---|---|---|---|---|---|---|---|---|
| AAA | GGC | TAC | CAC | TTG | GTC | TAC | AGC | CCC | CAG | GAT | GGC | GTC | ACC | TGT | GTG | 1968 |
| Lys | Gly | Tyr | His | Leu | Val | Tyr | Ser | Pro | Gln | Asp | Gly | Val | Thr | Cys | Val | |
| | | | | 645 | | | | | 650 | | | | | 655 | | |
| TCC | CCA | TGT | AGT | GAG | GGC | TAC | TGT | CAC | AAT | GGA | GGC | CAA | TGC | AAG | CAC | 2016 |
| Ser | Pro | Cys | Ser | Glu | Gly | Tyr | Cys | His | Asn | Gly | Gly | Gln | Cys | Lys | His | |
| | | | 660 | | | | | 665 | | | | | 670 | | | |
| CTG | CCA | GAT | GGG | CCC | CAG | TGC | ACG | TGC | GCA | ACC | TTC | AGC | ATC | TAC | ACA | 2064 |
| Leu | Pro | Asp | Gly | Pro | Gln | Cys | Thr | Cys | Ala | Thr | Phe | Ser | Ile | Tyr | Thr | |
| | | 675 | | | | | 680 | | | | | 685 | | | | |
| TCC | TGG | GGC | GAA | CGC | TGT | GAG | CAT | CTA | AGC | GTG | AAA | CTT | GGG | GCA | TTC | 2112 |
| Ser | Trp | Gly | Glu | Arg | Cys | Glu | His | Leu | Ser | Val | Lys | Leu | Gly | Ala | Phe | |
| | 690 | | | | | 695 | | | | | 700 | | | | | |
| TTC | GGG | ATC | CTC | TTT | GGA | GCC | CTG | GGT | GCC | CTC | TTG | CTA | CTG | GCC | ATC | 2160 |
| Phe | Gly | Ile | Leu | Phe | Gly | Ala | Leu | Gly | Ala | Leu | Leu | Leu | Leu | Ala | Ile | |
| 705 | | | | 710 | | | | | 715 | | | | | 720 | | |
| TTA | GCA | TGT | GTG | GTC | TTT | CAC | TTC | TGC | GGC | TGC | TCC | ATG | AAC | AAG | TTC | 2208 |
| Leu | Ala | Cys | Val | Val | Phe | His | Phe | Cys | Gly | Cys | Ser | Met | Asn | Lys | Phe | |
| | | | | 725 | | | | | 730 | | | | | 735 | | |
| TCC | TAC | CCT | CTG | GAC | TCA | GAA | CTG | | | | | | | | | 2232 |
| Ser | Tyr | Pro | Leu | Asp | Ser | Glu | Leu | | | | | | | | | |
| | | | 740 | | | | | | | | | | | | | |

( 2 ) INFORMATION FOR SEQ ID NO:98:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:98:

Glu  Phe  Cys  Gln  Asn  His  Ser  Cys
  1                    5

( 2 ) INFORMATION FOR SEQ ID NO:99:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:99:

Pro  Val  Asn  Tyr  Cys  Tyr  Asn  His  Gly  His  Cys  Asp  Ile  Ser  Gly  Pro
  1                    5                        10                      15

Pro  Asp ( 2 ) INFORMATION FOR SEQ ID NO:100:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:100:

Cys  Gln  Pro  Thr  Cys  Thr  Cys  Ala  Pro
  1                    5

( 2 ) INFORMATION FOR SEQ ID NO:101:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:101:

Ala Phe Thr Gly Asn Arg Cys Phe Leu Ala Gly Asn Asn
1               5                   10

( 2 ) INFORMATION FOR SEQ ID NO:102:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:102:

Gly Val Thr Cys Val Ser Pro Cys
1               5

( 2 ) INFORMATION FOR SEQ ID NO:103:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:103:

Ser Glu Gly Tyr Cys His Asn Gly Gly Gln Cys Lys His Leu Pro Asp
1               5                   10                  15

Gly Pro Gln ( 2 ) INFORMATION FOR SEQ ID NO:104:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:104:

Cys Thr Cys Ala Thr Phe Ser Ile Tyr Thr Ser Trp Gly Glu Arg Cys
1               5                   10                  15

Glu His Leu Ser Val Lys
                20

( 2 ) INFORMATION FOR SEQ ID NO:105:

( i ) SEQUENCE CHARACTERISTICS:
    ( A ) LENGTH: 33 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:105:

```
Cys Xaa Xaa Xaa Xaa Xaa Xaa Tyr Cys Leu Xaa Xaa Gly Xaa Cys Xaa
1               5                   10                  15

Xaa Xaa Xaa Xaa Xaa Xaa Xaa Xaa Xaa Xaa Xaa Xaa Cys Xaa Cys Xaa
                20                  25                  30

Xaa
```

(2) INFORMATION FOR SEQ ID NO:106:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

```
Gly Tyr Xaa Gly Xaa Arg Cys Xaa Xaa Xaa Xaa Leu Xaa
1               5                   10
```

(2) INFORMATION FOR SEQ ID NO:107:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

```
Glu Phe Cys Gln Asn His Ser Cys
1               5
```

(2) INFORMATION FOR SEQ ID NO:108:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:108:

```
Pro Val Asn Tyr Cys Tyr Asn His Gly His Cys Asp Ile Ser Gly Pro
1               5                   10                  15

Pro Asp Cys Gln Pro Thr
                20
```

(2) INFORMATION FOR SEQ ID NO:109:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:109:

```
Cys Thr Cys Ala Pro Ala Phe Thr Gly Asn Arg Cys Phe Leu Ala Gly
1               5                   10                  15

Asn Asn Phe
```

(2) INFORMATION FOR SEQ ID NO:110:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:110:

```
Gly Thr Ser His Leu Ile Lys Cys Ala Glu Lys Glu Lys Thr Phe Cys
  1               5                  10                  15
Val Asn Gly Gly Glu Cys Phe Thr Val Lys Asp Leu Ser Asn Pro Ser
             20                  25                  30
Arg Tyr Leu Cys Lys Cys Gln Pro Gly Phe Thr Gly Ala Arg Cys Thr
         35                  40                  45
Glu Asn Val Pro Met Lys
         50
```

( 2 ) INFORMATION FOR SEQ ID NO:111:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:111:

```
Gly Thr Ser His Leu Val Lys Cys Ala Glu Lys Glu Lys Thr Phe Cys
  1               5                  10                  15
Val Asn Gly Gly Glu Cys Phe Met Val Lys Asp Leu Ser Asn Pro Ser
             20                  25                  30
Arg Tyr Leu Cys Lys Cys Gln Pro Gly Phe Thr Gly Ala Arg Cys Thr
         35                  40                  45
Glu Asn Val Pro Met Lys
         50
```

( 2 ) INFORMATION FOR SEQ ID NO:112:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:112:

```
Gly Thr Ser His Leu Val Lys Cys Ala Glu Lys Glu Lys Thr Phe Cys
  1               5                  10                  15
Val Asn Gly Gly Glu Cys Phe Met Val Lys Asp Leu Ser Asn Pro Ser
             20                  25                  30
Arg Tyr Leu Cys Lys Cys Pro Asn Glu Phe Thr Gly Asp Arg Cys Gln
         35                  40                  45
Asn Tyr Val Met Ala Ser
         50
```

( 2 ) INFORMATION FOR SEQ ID NO:113:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:113:

Gly Thr Ser His Leu Thr Lys Cys Asp Ile Lys Gln Lys Ala Phe Cys
1               5                   10                  15

Val Asn Gly Gly Glu Cys Tyr Met Val Lys Asp Leu Pro Asn Pro Pro
            20              25                  30

Arg Tyr Leu Cys Arg Cys Pro Asn Glu Phe Thr Gly Asp Arg Cys Gln
        35              40                  45

Asn Tyr Val Met Ala Ser
        50

( 2 ) INFORMATION FOR SEQ ID NO:114:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:114:

Gly Val Thr Cys Val Ser Pro Cys Ser Glu
1               5                   10

( 2 ) INFORMATION FOR SEQ ID NO:115:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:115:

Gly Tyr Cys His Asn Gly Gly Gln Cys
1               5

( 2 ) INFORMATION FOR SEQ ID NO:116:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:116:

Lys His Leu
1

( 2 ) INFORMATION FOR SEQ ID NO:117:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:117:

Pro Asp Gly Pro Gln Cys Thr Cys Ala Thr Phe Ser Ile Tyr Thr Ser
1               5                   10                  15

```
    Trp Gly Glu Arg Cys
             20
```

(2) INFORMATION FOR SEQ ID NO:118:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:118:

```
    Glu His Leu Ser Val Lys
    1                5
```

(2) INFORMATION FOR SEQ ID NO:119:

(i) SEQUENCE CHARACTERISTICS:
  (A) LENGTH: 38 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:119:

```
    Gly Thr Ser His Leu Ile Lys Cys Ala Glu Lys Glu Lys Thr Phe Cys
    1                5                   10                      15
    Val Asn Gly Gly Glu Cys Phe Thr Val Lys Asp Leu Ser Asn Pro Ser
                    20                  25                  30
    Arg Tyr Leu Cys Lys Cys
                    35
```

(2) INFORMATION FOR SEQ ID NO:120:

(i) SEQUENCE CHARACTERISTICS:
  (A) LENGTH: 5 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:120:

```
    Gln Pro Gly Phe Thr
    1                5
```

(2) INFORMATION FOR SEQ ID NO:121:

(i) SEQUENCE CHARACTERISTICS:
  (A) LENGTH: 11 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:121:

```
    Gly Ala Arg Cys Thr Glu Asn Val Pro Met Lys
    1                5                   10
```

(2) INFORMATION FOR SEQ ID NO:122:

(i) SEQUENCE CHARACTERISTICS:
  (A) LENGTH: 38 amino acids
  (B) TYPE: amino acid (C) STRANDEDNESS: single
(D) TOPOLOGY: linear (ii) MOLECULE TYPE: peptide (xi) SEQUENCE DESCRIPTION: SEQ ID NO:122:

```
Gly Thr Ser His Leu Val Lys Cys Ala Glu Lys Glu Lys Thr Phe Cys
1               5                   10                  15
Val Asn Gly Gly Glu Cys Phe Met Val Lys Asp Leu Ser Asn Pro Ser
            20                  25                  30
Arg Tyr Leu Cys Lys Cys
            35
```

(2) INFORMATION FOR SEQ ID NO:123:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:123:

```
Pro Asn Glu Phe Thr
1               5
```

(2) INFORMATION FOR SEQ ID NO:124:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:124:

```
Gly Asp Arg Cys Gln Asn Tyr Val Met Ala Ser
1               5                   10
```

(2) INFORMATION FOR SEQ ID NO:125:

(i) SEQUENCE CHARACTERISTICS:
      (A) LENGTH: 38 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:125:

```
Gly Thr Ser His Leu Thr Lys Cys Asp Ile Lys Gln Lys Ala Phe Cys
1               5                   10                  15
Val Asn Gly Gly Glu Cys Tyr Met Val Lys Asp Leu Pro Asn Pro Pro
            20                  25                  30
Arg Tyr Leu Cys Arg Cys
            35
```